United States Patent
Rapoport et al.

(10) Patent No.: US 10,099,026 B2
(45) Date of Patent: Oct. 16, 2018

(54) SYSTEM, APPARATUS AND METHOD FOR SUPPLYING GASES

(75) Inventors: David M. Rapoport, New York, NY (US); Donald Roy Kuriger, Auckland (NZ); Mark John Arrowsmith, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 911 days.

(21) Appl. No.: 13/991,131

(22) PCT Filed: Dec. 2, 2011

(86) PCT No.: PCT/US2011/063137
§ 371 (c)(1), (2), (4) Date: Sep. 17, 2013

(87) PCT Pub. No.: WO2012/075433
PCT Pub. Date: Jun. 7, 2012

(65) Prior Publication Data
US 2014/0000610 A1    Jan. 2, 2014

Related U.S. Application Data

(60) Provisional application No. 61/419,421, filed on Dec. 3, 2010.

(51) Int. Cl.
*A61M 16/20* (2006.01)
*A61M 16/00* (2006.01)
(Continued)

(52) U.S. Cl.
CPC .... *A61M 16/0057* (2013.01); *A61M 16/0066* (2013.01); *A61M 16/0069* (2014.02);
(Continued)

(58) Field of Classification Search
CPC ........ A61B 5/4818; A61F 5/56; A61M 16/00; A61M 16/0051; A61M 16/0063;
(Continued)

(56) References Cited

U.S. PATENT DOCUMENTS 4,991,623 A * 2/1991 Ericson .................. E03C 1/122
137/216.2
5,503,146 A * 4/1996 Froehlich ............ A61M 16/024
128/202.22
(Continued)

FOREIGN PATENT DOCUMENTS

CN    1835775 A    9/2006
CN    1901962 A    1/2007
(Continued)

OTHER PUBLICATIONS

Office Action in Chinese Patent Application No. 201180064696.9, dated Feb. 2, 2015 in 12 pages.
(Continued)

*Primary Examiner* — Annette Dixon
(74) *Attorney, Agent, or Firm* — Knobbe, Martens, Olson & Bear, LLP

(57) ABSTRACT

A system, apparatus and methods are provided for supplying gases to a user. The supply includes a sub-therapeutic mode and a pressure support mode for delivering therapy to a user. A flow diversion device or valve switches from a first mode corresponding with the sub-therapeutic mode of the system to a second mode corresponding with the pressure support mode of the system. In the first mode, the valve opens a larger flow path between the interior of the user interface and ambient air than in the second mode.

22 Claims, 20 Drawing Sheets

(51) Int. Cl.
*A61M 16/08* (2006.01)
*A61M 16/10* (2006.01)
*A61M 16/16* (2006.01)

(52) U.S. Cl.
CPC ...... *A61M 16/0816* (2013.01); *A61M 16/109* (2014.02); *A61M 16/20* (2013.01); *A61M 16/208* (2013.01); *A61M 16/16* (2013.01); *A61M 2016/0027* (2013.01); *A61M 2016/0039* (2013.01); *A61M 2205/3653* (2013.01); *A61M 2205/502* (2013.01)

(58) Field of Classification Search
CPC .......... A61M 16/0066; A61M 16/0069; A61M 16/024; A61M 16/06; A61M 16/0858; A61M 16/0883; A61M 16/10; A61M 16/101; A61M 16/107; A61M 16/1075; A61M 16/109; A61M 16/12; A61M 16/16; A61M 16/20; A61M 16/202; A61M 16/204; A61M 16/205; A61M 16/206; A61M 16/208; A61M 16/22; A61M 2016/0015; A61M 2016/0021; A61M 2016/0027; A61M 2016/003; A61M 2016/0036; A61M 2016/0039; A61M 2016/0042; A61M 2205/14; A61M 2205/15; A61M 2205/3303; A61M 2205/3334; A61M 2205/3355; A61M 2205/3358; A61M 2205/3365; A61M 2205/3553; A61M 2205/3584; A61M 2205/42; A61M 2205/50; A61M 2205/52; A61M 2205/6054; A61M 2205/702; A61M 2230/40; A61M 2230/42
USPC ............ 128/202.22, 204.18, 204.21, 204.22, 128/204.23, 204.26, 205.24, 205.25
See application file for complete search history.

(56) References Cited

U.S. PATENT DOCUMENTS

| | | | | |
|---|---|---|---|---|
| 5,551,419 | A * | 9/1996 | Froehlich | A61M 16/024 128/204.23 |
| 5,839,436 | A * | 11/1998 | Fangrow, Jr. | A62B 9/02 128/204.18 |
| 5,937,855 | A * | 8/1999 | Zdrojkowski | A61M 16/20 128/204.23 |
| 6,062,248 | A * | 5/2000 | Boelkins | F16K 15/148 137/118.02 |
| 6,186,477 | B1 * | 2/2001 | McCombs | A61M 16/20 128/205.24 |
| 6,988,994 | B2 | 1/2006 | Rapoport et al. | |
| 7,044,129 | B1 * | 5/2006 | Truschel | A61M 16/12 128/204.18 |
| 7,168,429 | B2 * | 1/2007 | Matthews | A61M 16/0051 128/204.21 |
| 7,798,143 | B1 * | 9/2010 | Kirby | A61M 16/00 128/204.18 |
| 8,439,035 | B2 * | 5/2013 | Dantanarayana | A61B 5/0876 128/203.11 |
| 9,027,553 | B2 * | 5/2015 | Witt | A61M 16/0666 128/205.25 |
| 9,314,579 | B2 * | 4/2016 | McDaniel | A61M 16/0051 |
| 9,750,908 | B2 * | 9/2017 | Kuriger | A61M 16/0051 |
| 2003/0005931 | A1 * | 1/2003 | Jaffre | A61M 16/08 128/204.18 |
| 2004/0129270 | A1 * | 7/2004 | Fishman | A61M 16/0051 128/204.18 |
| 2007/0113849 | A1 * | 5/2007 | Matthews | A61M 16/0051 128/204.22 |
| 2008/0047426 | A1 * | 2/2008 | Dolensky | A62B 21/00 95/22 |
| 2008/0092894 | A1 | 4/2008 | Nicolazzi et al. | |
| 2008/0097234 | A1 | 4/2008 | Nicolazzi et al. | |
| 2010/0126506 | A1 * | 5/2010 | Kepler | A61M 16/0051 128/203.12 |
| 2011/0259331 | A1 * | 10/2011 | Witt | A61M 16/0666 128/204.18 |
| 2011/0259334 | A1 | 10/2011 | Alfieri et al. | |
| 2011/0259340 | A1 * | 10/2011 | Witt | A61M 16/0666 128/207.18 |
| 2012/0065533 | A1 | 3/2012 | Carrillo, Jr. et al. | |
| 2012/0111311 | A1 * | 5/2012 | Steck | F24C 3/14 126/81 |
| 2012/0227742 | A1 * | 9/2012 | Witt | A61M 16/0666 128/205.24 |
| 2014/0096774 | A1 | 4/2014 | Olsen et al. | |
| 2014/0283842 | A1 | 9/2014 | Bearne et al. | |
| 2016/0015918 | A1 | 1/2016 | Kuriger et al. | |

FOREIGN PATENT DOCUMENTS

| | | | |
|---|---|---|---|
| EP | 0788805 A2 | 1/2007 | |
| WO | WO 1992/011054 A1 | 7/1992 | |
| WO | WO 2005/063326 | 7/2005 | |
| WO | WO 2008/039979 | 4/2008 | |
| WO | WO 2010/044036 | 4/2010 | |
| WO | WO 2010076712 A1 * | 7/2010 | ........ A61M 16/0666 |
| WO | WO 2010/140072 | 9/2010 | |
| WO | WO 2012/006339 | 1/2012 | |
| WO | WO 2012/020314 | 2/2012 | |
| WO | WO 2012/075433 A3 | 6/2012 | |
| WO | WO 2012/140514 | 10/2012 | |
| WO | WO 2013/066195 | 10/2013 | |
| WO | WO 2014/007659 A1 | 1/2014 | |

OTHER PUBLICATIONS

International Preliminary Report on Patentability in PCT Application No. PCT/US2011/063137, dated Jun. 13, 2013 in 7 pages.
International Search Report; PCT/US2013/000014; dated Sep. 24, 2013 in 7 pages.
International Search Report; PCT/US2011/063137; dated Jun. 22, 2012; 3 pages.
Written Opinion; PCT/US2011/063137; dated Jun. 22, 2012; 6 pages.
Patent Examination Report in Application No. GB 1310564.8 dated Feb. 18, 2016 in 5 pages.
Patent Examination Report in Australian Application No. 2011336371, dated Jun. 29, 2015 in 3 pages.
Supplementary Search Report; PCT/US2013/000014; dated Jul. 23, 2015 in 7 pages.
Patent Examination Report in Canadian Application No. 2819647, dated Oct. 18, 2017 in 4 pages.

* cited by examiner US 10,099,026 B2

SYSTEM, APPARATUS AND METHOD FOR SUPPLYING GASES

CROSS-REFERENCE TO RELATED APPLICATIONS

This application is a national phase of International Application No. PCT/US2011/063137 filed Dec. 2, 2011 which claims the priority benefit under 35 U.S.C. § 119(e) of U.S. Provisional Application No. 61/419,421, filed on Dec. 3, 2010, the entireties of which are hereby incorporated by reference herein in its entirety.

BACKGROUND OF THE INVENTION

Field of the Invention

The present invention generally relates to apparatus and methods for supplying respiratory gas under positive pressure to a sleeping user, such as in the treatment of obstructive sleep apnea (OSA). More particularly, the present invention relates to such apparatus and methods in which a condition of a user's body is sensed. Even more particularly, the present invention relates to such apparatus and methods featuring a gas supply that is responsive to breathing and that includes a valve in the control mechanism.

Description of the Related Art

A common method of treating obstructive sleep apnea (OSA) involves a pressure device that provides breathing gases, typically air, to a user (often referred to as the patient) while the user is asleep. These machines fall into the broad classification of PAP (positive airway pressure) devices or CPAP (continuous PAP) devices.

Within this broad classification, there are wide variations. For example, some machines provide different pressure during user inspiration than during user expiration (Bi PAP), some machines provide an auto-setting or autotitrating mode, wherein the supplied pressure varies through the period of use in response to detected events. In this context, detected events may include snoring, hypopneas and obstructive breathing. Some machines respond to user awakening and mask removal, for example, by reducing the delivered pressure. Some machines deliver a predetermined set pressure, which may be delivered at the same pressure night after night or which may be varied night by night by physical adjustment or by automatic adjustment by the unit. Some machines include a ramp function that begins automatically or that begins by user selection. The ramp function causes the machine to commence operation at a low pressure, which is sometimes settable, and to gradually increase to a higher pressure, which may be a predetermined treatment pressure or which may be an intermediate pressure.

The machines typically provide controlled pressure delivery. For example, the machines typically include a flow generator, a pressure sensor that senses the pressure being delivered to the user, and a feedback control that controls the output of the flow generator based upon a sensor signal so that the sensed pressure is maintained close to a demand pressure. Alternatively, the flow generator may include a fan that generates a known pressure and flow response. The output of the flow generator can be controlled to deliver a desired pressure using feedback from a flow sensor in a circuit that is connected to the flow generator. Alternatively, the flow generator may include a fan that provides a substantially uniform pressure at a given rotation speed across a useful range of flow. Pressure then can be controlled by setting a constant motor speed.

Even for the lower pressure at the start of a ramp cycle, most of the machines supply a minimum pressure of 3 cmH2O or more. The minimum pressure is more comfortable for the user than the full treatment pressure and results in a sufficient flow of breathing gases through a supply line to the user so that breathing gases exit through a bias flow or a controlled leak port provided at or near a user interface that is connected to the supply line.

SUMMARY OF THE INVENTION

An object of the present invention is to provide apparatus or method for providing breathing gases to a user, which at least go someway toward improving on prior systems, or which will at least provide users with a useful choice.

In some configurations, an apparatus comprises a flow generator and a controller connected to control the output of the flow generator. A conduit extends from the flow generator to connect with a user interface with the inside of the conduit and the inside of the user interface defining a gases space. A valve positioned at or adjacent the user interface. The valve being switchable between a first mode in which the gases space is significantly open to ambient through the valve and a second mode in which the gases space is not significantly open to ambient through the valve. The controller including one or more positive airway pressure support modes in which the controller may cause the flow generator to deliver pressure support to the airway of a user with the valve in the second mode and the controller including one or more sub-therapeutic modes in which the controller may cause the flow generator to deliver flow of gases to the user with the valve in the first mode.

The valve can include an aperture that communicates the gases space with ambient and a valve member that, in a second position, closes the aperture and is substantially out of the flow path of gases through the conduit or interface and, in a first position, leaves the aperture open for substantially unimpeded flow from the interface to the ambient.

In the first position, the valve member may partially, but not fully, occlude flow from the flow generator to the interface. In some configurations, the first position of the valve comprises the valve being bent towards the user when the user is inhaling. In some configurations, the first position of the valve comprises the valve being bent toward the flow generator when the user is exhaling.

The valve member when in the first position preferably occludes between about 50% and about 80% of a cross-sectional area of a flow path from the flow generator to the user interface.

The positive airway pressure support modes can include a supply of gases to a user such that, with the valve in the first mode, the flow generator provides enough flow to the user interface such that with the interface worn by a user a pressure greater than about 3 cm H2O is produced.

A sensor can be included to derive a measure of pressure in the gases space such that in a positive airway pressure mode the controller controls output of the flow generator according to a command pressure and feedback from the sensor for deriving the measure of pressure in the gases space.

In some configurations, in the sub-therapeutic mode, the controller provides a flow to the interface that is not sufficient to force the valve into the closed position.

In the sub-therapeutic mode, the controller can cause flow generator to provide a flow greater than about 5 liters per minute (most preferably greater than about 10 liters per minute).

In some configurations, in the sub-therapeutic mode, the controller causes the flow generator to provide a flow less than about 20 liters per minute (most preferably less than 15 liters per minute).

The valve can move from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve can remain stable for flows up to at least about 20 liters per minute, with delivered pressures below about 2 cm H2O.

With the valve in the second mode, and the controller operating in the pressure support mode, the valve can remain stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 liters per minute.

In some configurations, in the sub-therapeutic mode, the controller controls the flow generator to deliver an average flow at a level that assures flushing of the user interface but which does not trigger the valve to switch from the first mode to the second mode.

In some configurations, the controller controls the flow generator to provide an average flow over multiple breaths that is substantially constant.

In some configurations, an apparatus comprises a flow generator and a controller connected to control the output of the flow generator. A conduit extends from the flow generator to connect with a user interface. The inside of the user interface defines a gases space. A valve at or adjacent the user interface is switchable between a first mode, in which the gases space is open to ambient through the valve, and a second mode, in which the gases space generally is not open to ambient through the valve. Control of the flow generator and the construction and arrangement of the valve can be such that in a period of transition (in either direction) between a pressure support delivery to the user and a sub-therapeutic supply to the user, user breathing does not trigger repeated cycling between the first mode and the second mode.

The controller can include one or more positive airway pressure support modes in which the controller may cause the flow generator to deliver pressure support to the airway of a user with the valve in the second mode and one or more sub-therapeutic modes in which the controller may cause the flow generator to deliver flow of gases to the user with the valve in the first mode.

In some configurations, the one or more positive airway pressure modes include supply of gases to the user such that, with the valve in the closed position, the flow generator provides enough flow to the user interface such that, with the interface worn by a user, a pressure greater than about 3 cm H2O is produced.

A sensor can be provided to derive a measure of pressure in the gases space wherein, in a positive airway pressure mode, the controller controls the output of the flow generator according to a command pressure and feedback of the measure of pressure in the gases space from the sensor.

In some configurations, in the sub-therapeutic mode, the controller provides a flow to the interface that is not sufficient to force the valve into the first mode.

In some configurations, in the sub-therapeutic mode, the controller causes the flow generator to provide a flow greater than about 5 liters per minute (most preferably greater than about 10 liters per minute).

In some configurations, in the sub-therapeutic mode, the controller causes the flow generator to provide a flow less than about 20 liters per minute (most preferably less than about 15 liters per minute).

In some configurations, in the sub-therapeutic mode, the controller controls the flow generator to deliver an average flow at a level that assures flushing of the user interface, but which does not trigger the valve to switch from the first mode to the second mode.

The controller can control the flow generator to provide an average flow over multiple breaths that is substantially constant.

The valve can include an aperture communicating the gases space with ambient and a valve member that in a first position closes the aperture and is out of the flow path of gases through the conduit or interface and in a second position leaves the aperture open for substantially unimpeded flow from the interface to the ambient.

In some configurations, in the second position, the valve member partially, but not fully, occludes flow from the flow generator to the interface.

In some configurations, in the second position, the area valve member occludes between about 50% and about 80% of a cross sectional area of a flow path from the flow generator to the user interface.

In some configurations, the valve moves from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve remains stable for flows up to at least about 20 liters per minute with delivered pressures below about 2 cm H2O.

In some configurations, with the valve in the second mode and the controller operating in the pressure support mode, the valve remains stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 liters per minute.

In some configurations, an apparatus comprises a flow generator, a controller connected to control the output of the flow generator, and a conduit extending from the flow generator to connect with a user interface with the inside of the conduit and the inside of the user interface defining a gases space. A valve can be positioned at or adjacent the user interface and can include an aperture communicating the gases space with ambient and a valve member wherein, in a first position, the valve member leaves the aperture substantially open for flow from the interface to the ambient and, in a second position, the valve member closes the aperture, and wherein the valve member moves from the first position to the second position upon rising through a first threshold of flow/pressure, and from the second position to the first position on falling through a second threshold of flow/pressure, wherein the first threshold of flow/pressure is higher than the second threshold of flow/pressure.

The controller can include one or more positive airway pressure support modes in which the controller causes the flow generator to deliver pressure support to the airway of a user with the valve in the second mode and one or more sub-therapeutic modes in which the controller causes the flow generator to deliver flow of gases to the user with the valve in the first mode.

The positive airway pressure modes can include supply of gases to the user such that, with the valve in the closed position, the flow generator provides enough flow to the user interface such that, with the interface worn by a user, a pressure greater than about 3 cm H2O is produced.

A sensor can be provided to obtain a measure of pressure in the gases space such that, in a positive airway pressure mode, the controller controls the output of the flow generator according to a command pressure and feedback of the measure of pressure in the gases space from the sensor.

In some configurations, in the sub-therapeutic mode, the controller provides a flow to the interface that is not sufficient to force the valve into the closed position.

In some configurations, in the sub-therapeutic mode, the controller causes the flow generator to provide a flow greater than about 5 liters per minute (most preferably greater than about 10 liters per minute).

In some configurations, in the sub-therapeutic mode, the controller causes the flow generator to provide a flow less than about 20 liters per minute (most preferably less than about 15 liters per minute).

In some configurations, in the sub-therapeutic mode, the controller controls the flow generator to deliver an average flow at a level that assures flushing of the user interface but which does not trigger the valve to switch from the first position to the second position.

In some configurations, the controller controls the flow generator to provide an average flow over multiple breaths that is substantially constant.

In some configurations, with the valve in the first position and the controller operating in the sub-therapeutic mode, the valve remains stable for flows up to at least about 20 liters per minute with delivered pressures below about 2 cm H2O.

In some configurations, with the valve in the second position and the controller operating in the pressure support mode, the valve remains stable at pressures down to about 3 cm H2O or lower.

In some configurations, the lowest pressure for which the valve is stable in the second position when the controller is in the pressure support mode is less than about 1 cm H2O above the average delivered pressure when the valve is in the first position and the controller is in the sub-therapeutic mode supplying about 15 liters per minute.

In some configurations, in the second position, the valve member partially, but not fully, occludes flow from the flow generator to the interface.

In some configurations, in the second position, the valve member occludes between about 50% and about 80% of a cross sectional area of a flow path from the flow generator to the user interface.

In some configurations, an apparatus comprises a flow generator, a controller connected to control the output of the flow generator, and a nasal mask for covering nasal passages of a wearer but leaving a mouth uncovered. A conduit extends from the flow generator to connect with the nasal mask with the inside of the conduit and the inside of the nasal mask defining a gases space. A valve is positioned at or adjacent the nasal mask which is switchable between a first mode, where the gases space is open to ambient through the valve, and a second mode, where the gases space is not open to ambient through the valve. The controller controls the flow generator to deliver gases through the conduit with the valve in the first mode and with the valve in the second mode.

The controller can include one or more positive airway pressure support modes in which the controller may cause the flow generator to deliver pressure support to the airway of a user with the valve in the second mode, and one or more sub-therapeutic modes in which the controller may cause the flow generator to deliver flow of gases to the user with the valve in the first mode.

The positive airway pressure modes can include supply of gases to the user such that, with the valve in the first mode, the flow generator provides enough flow to the user interface such that, with the interface worn by a user, a pressure greater than 3 cm H2O is produced.

A sensor can be provided for deriving a measure of pressure in the gases space where, in a positive airway pressure mode, the controller controls the output of the flow generator according to a command pressure and feedback of the measure of pressure in the gases space.

In some configurations, in the sub-therapeutic mode, the controller provides a flow to the interface that is not sufficient to force the valve into the second mode.

In some configurations, in the sub-therapeutic mode, the controller causes the flow generator to provide a flow greater than about 5 liters per minute (most preferably greater than about 10 liters per minute).

In some configurations, in the sub-therapeutic mode, the controller causes the flow generator to provide a flow less than about 20 liters per minute (most preferably less than about 15 liters per minute).

In some configurations, in the sub-therapeutic mode, the controller controls the flow generator to deliver an average flow at a level that assures flushing of the user interface but that does not trigger the valve to switch from the first mode to the second mode.

In some configurations, the controller controls the flow generator to provide an average flow over multiple breaths that is substantially constant.

In some configurations, the valve includes an aperture communicating the gases space with ambient and a valve member that is moveable between a first position corresponding to the second mode and a second position corresponding to the first mode, the valve member in the first position closing the aperture and being positioned out of the flow path of gases between the valve inlet and the valve outlet, and the valve member in a second position leaving the aperture open for substantially unimpeded flow from the valve inlet to ambient.

In some configurations, in the second position, the valve member partially, but not fully, occludes flow from the valve inlet to the valve outlet.

In some configurations, in the second position, the valve member occludes between about 50% and about 80% of a cross sectional area of a flow path from the valve inlet to the valve outlet.

In some configurations, the valve moves from the first mode to the second mode upon rising through a first threshold of flow/pressure, and from the second mode to the first mode on falling through a second threshold of flow/pressure, wherein the first threshold of flow/pressure is higher than the second threshold of flow/pressure.

In some configurations, with the valve in the first mode and the controller operating in the sub-therapeutic mode, the valve remains stable for flows up to at least about 20 liters per minute with delivered pressures below 2 cm H2O.

In some configurations, with the valve in the second mode and the controller operating in the pressure support mode, the valve remains stable at pressures down to about 3 cm H2O or lower.

In some configurations, the lowest pressure for which the valve is stable in the second mode when the controller is in the pressure support mode is less than about 1 cm H2O above the average delivered pressure when the valve is in the first mode and the controller is in the sub-therapeutic mode supplying about 15 liters per minute.

A valve can be provided for use at or adjacent a user interface. The valve comprises a flow passage defined by at least one wall. The flow passage extends between a valve inlet and a valve outlet configured to open toward the user interface. An aperture through the at least one wall defines the flow passage. The aperture is positioned between the valve inlet and the valve outlet with a valve member being positioned between the valve inlet and the aperture. The valve member is movable between a first position and a second position. The valve member in the first position leaving the aperture open for flow from the interface to ambient and the valve member in the second position closing the aperture. The valve member is adapted to move from the first position to the second position upon rising through a first threshold of flow/pressure in the flow passage, and the valve member is adapted to move from the second position to the first position on falling through a second threshold of flow/pressure in the flow passage, wherein the first threshold of flow/pressure is higher than the second threshold of flow/pressure.

In some configurations, in the second position, the valve member partially, but not fully, occludes flow from the valve inlet to the valve outlet.

In some configurations, in the second position, the valve member occludes between 50% and 80% of a cross sectional area of a flow path from the valve inlet to the valve outlet.

A valve can be provided for use at or adjacent a user interface. The valve comprises a flow passage at least partially defined by a wall. The flow passage extends between a valve inlet and a valve outlet that is adapted to be fluidly connected to the user interface. An aperture is defined through the wall. The aperture is positioned between the valve inlet and the valve outlet with a valve member being positioned between the valve inlet and the aperture. The valve member is movable between a first position and a second position. When the valve member is in the first position, the aperture is left open for flow from the interface to ambient. When the valve member is in the first position, flow is partially but not fully occluded through the flow passage. When the valve member is in the second position, the aperture is substantially closed. The valve member in the first position occludes between about 50% and about 80% of a cross section area of a flow passage between the inlet and the outlet at the valve member.

In some configurations, a cross-sectional area of the flow passage through the valve at the valve member is between about 40 mm2 and about 250 mm2.

In some configurations, the area of the aperture is between about 10% and about 50% of the cross sectional area of the flow passage through the valve.

In some configurations, the area of the aperture is between about 15% and about 25% of the cross sectional area of the flow passage through the valve.

In some configurations, in the second position, the valve member partially, but not fully, occludes flow from the flow generator to the interface.

In some configurations, in the second position, the area valve member occludes between about 50% and about 80% of the area of the flow path from the flow generator to the user interface.

A valve can be provided for use at or adjacent a user interface. The valve comprises a flow passage defined by a wall. The flow passage extends between a valve inlet and a valve outlet. An aperture is defined through the wall. The aperture is positioned between the valve inlet and the valve outlet. A valve member is positioned between the valve inlet and the aperture. The valve member is movable between a first position and a second position, wherein the valve member in the first position leaving the aperture open for flow from the user interface to ambient, the valve member in the second position at least partially closing the aperture, and the valve member being stable in the first position under user breathing for average flows over multiple breaths of up to 30 liters per minute, delivering a pressure below about 1.5 cm H2O, and being stable in the second position under user breathing for controlled pressures above about 1.7 cm H2O.

In some configurations, a cross-sectional area of the flow passage through the valve from the inlet to the outlet is between about 350 mm2 and about 600 mm2.

In some configurations, the area of the aperture is between 10% and 50% of a cross-sectional area of the flow passage through the valve.

In some configurations, the area of the aperture is between 15% and 25% of the cross sectional area of the flow passage through the valve.

In some configurations, in the second position, the valve member partially, but not fully, occludes flow from the flow generator to the interface.

In some configurations, in the second position, the valve member occludes between about 50% and about 80% of a cross sectional area of the flow path from the flow generator to the user interface.

In some configurations, a system is provided for supplying respiratory gases to a user wearing a user interface. The system comprises a flow generator and a controller adapted to control operation of the flow generator. The flow generator has a flow control mode and a pressure control mode. The flow control mode comprises generation of a sub-therapeutic flow of gases and the pressure control mode comprises generation of a therapeutic flow of gases. A flow diversion valve is positioned between the flow generator and the user interface. The flow diversion valve comprises a flow channel and an aperture. The aperture places the flow channel in fluid communication with ambient. The flow diversion valve further comprises a valve member that is cantilevered from a wall and that extends toward the flow channel in a first position. The valve member is moveable between the first position and a second position. The valve member overlies at least a portion of the aperture in the second position and the valve member occludes only a portion of the flow channel in the first position. The valve member is movable from the first position to the second position when the flow generator transitions from the flow control mode to the pressure control mode and movable from the second position toward the first position when the flow generator transitions from the pressure control mode to the flow control mode.

In some configurations, the valve member does not abut a valve seat in the first position.

In some configurations, the valve member is in the first position when there is no flow through the flow channel and the valve member does not abut a valve seat in the first position. In some configurations, the first position of the valve comprises the valve being bent towards the user when the user is inhaling. In some configurations, the first position of the valve comprises the valve being bent toward the flow generator when the user is exhaling.

In some configurations, the valve member when in the first position occludes between about 50% and about 80% of a cross-sectional area of the flow channel.

In some configurations, the flow control mode comprises delivering an average flow rate of between about 15 liters per minute and about 17 liters per minute.

In some configurations, the flow control mode comprises delivering a pressure of less than about 4 centimeters water.

In some configurations, the valve member abuts a land in the second position.

In some configurations, the land is offset inwardly toward the flow channel from a portion of the valve member that is secured to a body of the valve.

In some configurations, the aperture defines an opening with a cross-sectional area of about 90 mm2.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The term "comprising" is used in the specification and claims, means "consisting at least in part of." When interpreting a statement in this specification and claims that includes "comprising," features other than that or those prefaced by the term may also be present. Related terms such as "comprise" and "comprises" are to be interpreted in the same manner.

BRIEF DESCRIPTION OF THE DRAWINGS

These and other features, aspects and advantages of the present invention will now be described with reference to the drawings of preferred embodiments, which embodiments are intended to illustrate and not to limit the invention, and in which figures.

DETAILED DESCRIPTION OF THE PREFERRED EMBODIMENT

Figure 1:
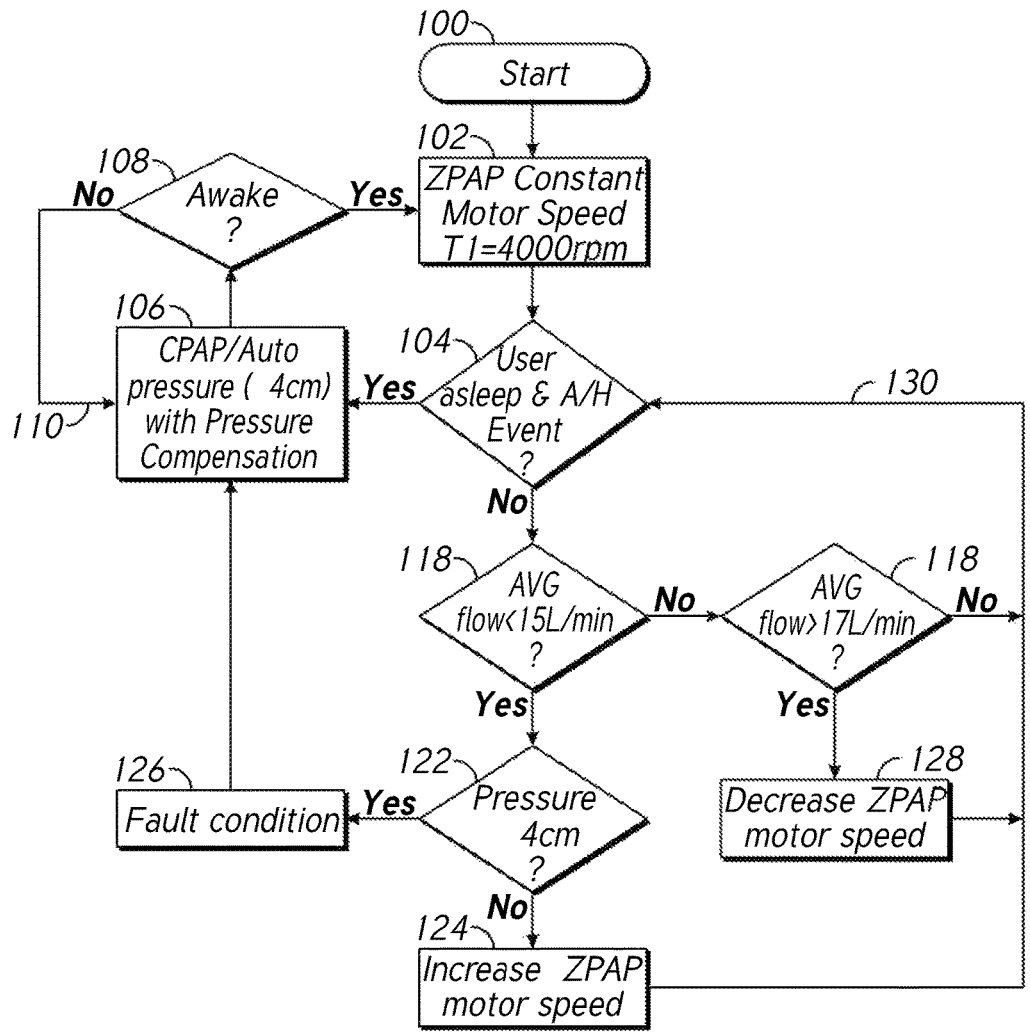
FIG. 1 is a flow diagram illustrating a control method that is arranged and configured in accordance with certain features, aspects and advantages of the present invention and that can be implemented by a controller of a gas supply apparatus.

The following description presents a system, and elements of that system, that can provide an alternative to a defined pressure ramp at the commencement of a treatment session. The system, and the elements of that system, also can provide an alternative to low therapeutic pressures (i.e., awake pressures) at other times when a user (i.e., user) is thought to be awake.

Certain features, aspects and advantages of the present invention relate to a sub-therapeutic control mode in which the user receives mask pressures that approach ambient or atmospheric pressure, which is referred to herein as "zero pressure." The use of zero pressure contrasts with traditional therapeutic CPAP, which maintains a therapeutic level of pressure at all times when therapy for obstructive sleep apnea is needed.

A sub-therapeutic control mode allows very low mask pressures at times when therapy is not needed, desired or intended. The very low mask pressures make using the system more pleasant for the user by removing unnecessary or undesired pressure wherever possible while reducing the likelihood of compromising other functions of the system (e.g., external venting to reduce the likelihood of CO2 rebreathing). Because of increased comfort produced by reduced perceived pressure when therapeutic airway support is not needed or not desired, the sub-therapeutic control mode is believed to encourage increased compliance, which will extend the time the user wears the system and receives therapeutic CPAP treatment.

A limiting factor in the implementation of sub-therapeutic gas delivery with existing CPAP machines is that substantially all systems currently used with CPAP machines rely on non-zero mask and circuit pressure to force air through a "leak port" throughout the respiratory cycle. The air forced out through the leak port provides venting of exhaled carbon dioxide, particularly during exhalation, and reduces the likelihood of rebreathing of exhaled gas during the next inspiration. When the mask and circuit pressure falls below a certain low level (e.g., generally around 2 cm H2O to 5 cm H2O depending upon the size of the leak port), venting through a fixed size leak port becomes generally ineffective.

Two types of valves that can be used in the system that is arranged and configured in accordance with certain features, aspects and advantages of the present invention are "non-rebreathing" valves and "exhalation valves." Each of the two types of valves creates a second port through which exhaled gas can be directed to reduce the likelihood of rebreathing. Non-rebreathing valves generally are passively opened when the relevant pressure is substantially zero or zero (e.g., when a gas supply apparatus has stopped functioning) or when flow reverses within a circuit. Exhalation valves also can be used in non-CPAP circuits and typically trigger from shut to open with rises in pressure during exhalation. Exhalation valves are often driven by an external triggering mechanism that detects expiration; however, when used during CPAP, the exhalation valves cannot be dependent on pressure at the valve alone because the pressure is high in both therapeutic CPAP and during exhalation. In addition, the valve must be actively triggered or driven by an outside controller. In some embodiments, the system can be implemented with specifically adapted valves having characteristics described later in this specification.

Some implementations of the sub-therapeutic mode utilize an external decision about which mode of the valve is active. At a predetermined point, which could be predicated on the desired CPAP pressure or on the state of arousal of a user, the controller adjusts the characteristics of the flow and pressure in the circuit to trigger an increase in the leak out of the circuit, such as, for example but without limitation, opening an additional port or otherwise creating an increase in leakage flow. In the therapeutic CPAP mode, the controller delivers gases at a flow and pressure such that the valve minimizes the size of the leak (e.g., by closing the additional port). Preferably, the change in valve behaviour occurs generally as a passive response of the valve but in response to some signal generated by an algorithm controlling CPAP delivery.

Preferably, the transition from the sub-therapeutic mode to the conventional therapy mode of operation (i.e., CPAP) happens in a substantially "smooth" fashion and does not significantly oscillate with respiratory swings. Thus, the mode change may be largely undetected or minimally intrusive to the user. One aspect of making the transition generally transparent to the user is minimizing the change in system conditions (e.g., pressure and flow) that activates the change in mode of operation of the valve while preserving the stability of the valve mode.

Certain features, aspects and advantages of the present invention relate to a valve with two modes. Certain features, aspects and advantages of the present invention relate to activating control of the valve mode through changes in the behaviour of the CPAP gas supply without other external control signals to the valve. Preferably, despite minimal change in pressure but at a desired time, the valve switches between an "open" state, a state with minimal pressure in the circuit and low but significant flow to the user, and a "closed" state, a state with pressure that can be raised to therapeutic levels, and the transition occurs with little or no change in the system conditions perceived by the user. In other words, the "open" state refers to the interior of the circuit being open to ambient surroundings through the valve while the "closed" state refers to a state where the valve does not allow the same substantial flow between inside the circuit and ambient through the valve. However, some flow between inside the circuit and ambient may be provided for in the closed state. For example, the valve may incorporate a bias flow vent to provide suitable leak during therapy.

Figure 2:
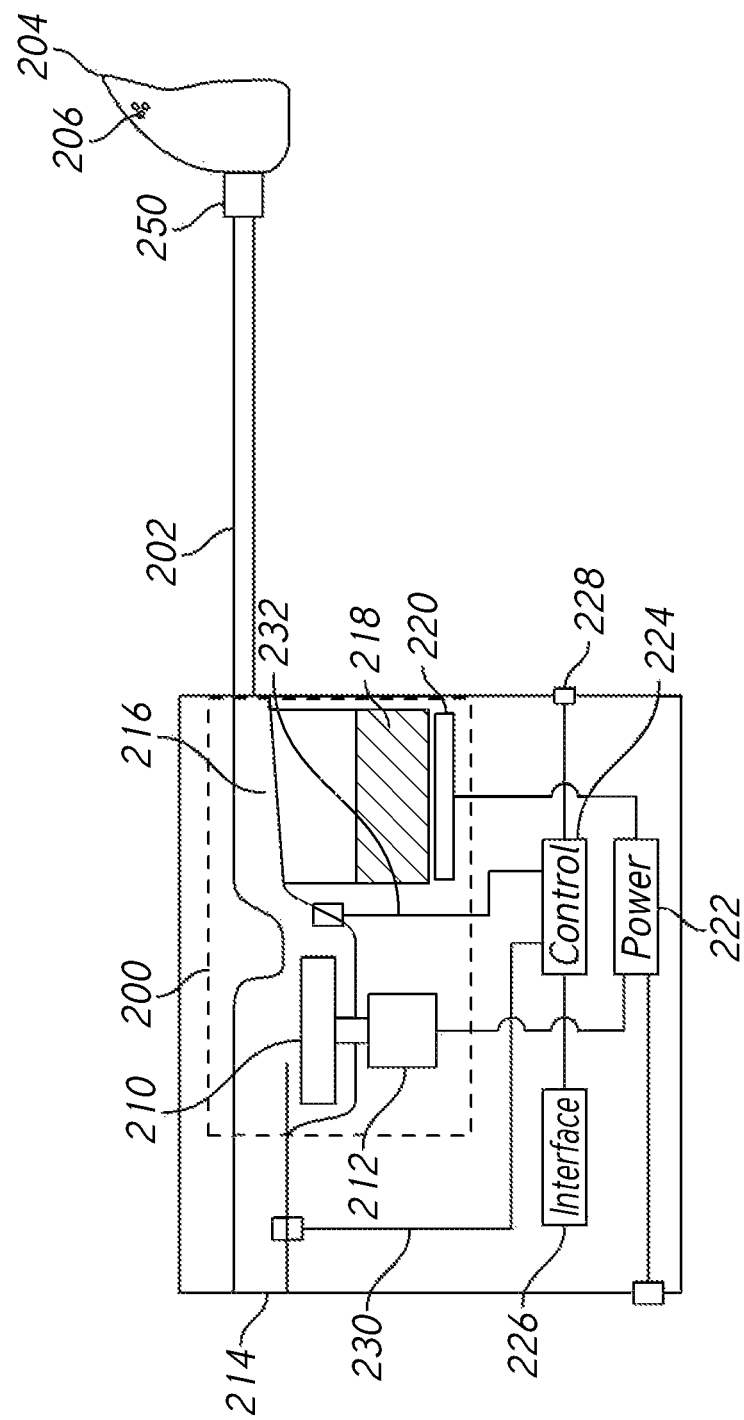
FIG. 2 is a block diagram illustrating a gases supply system that is arranged and configured in accordance with certain features, aspects and advantages of the present invention.

With reference to FIG. 2, the system generally comprises a gas supply device 200, a user interface 204, a supply conduit or tube 202 for connecting between the supply device 200 and the user interface 204 and a flow diversion device 250. The flow diversion device preferably is located at or generally adjacent to the user interface 204.

The flow diversion device 250 can operate in at least two modes. In some configurations, the flow diversion device 250 operates in only two modes. In a first mode, the gases space inside the user interface 204 is substantially open or open to ambient surroundings through the flow diversion device 250. In a second mode, the flow diversion device 250 allows the user to receive a gases flow at a therapeutic treatment pressure from the gases supply device 200.

Preferably, the flow diversion device 250 comprises a type of valve in which the valve 250 is in the first mode or condition at low pressure or flow conditions (i.e., sub-therapeutic supply conditions). In this condition, the interior of the user interface 204 is substantially open to ambient surroundings through the valve 250. In the second mode or condition, the valve 250 is closed and the gases space inside the user interface 204 is significantly less open to ambient surroundings through the valve 250.

Typically, the gases space inside the user interface 204 may be connected at all times with the ambient environment through a vent 206, such as a bias flow vent or other controlled leak port. For example, the vent 206 is illustrated in FIG. 2 on the user interface 204. In some configurations, the vent 206 may be part of the flow diversion device 250 itself.

Preferably, the flow path to ambient surroundings through the flow diversion device 250, with the valve in the first mode, is a path of much lower resistance than the flow path through the controlled leak provided through the vent 206. Thus, with the flow diversion device 250 in the first mode, the flow path between the gases supply device 200 and the gases space inside the user interface 204 is somewhat restricted but is not closed while a comparatively open flow path is provided between the gases space inside the user interface 204 and the surrounding ambient conditions through the flow diversion device 250. In the second mode, there is comparatively little or no flow between the gases space inside the user interface 204 and the surrounding ambient conditions through the flow diversion device 250 while the flow diversion device 250 presents a comparatively low flow restriction between the gases space inside the user interface 204 and the gases supply device 200.

Preferably, the control of the gases supply device 200 and the arrangement of the flow diversion device 250 (e.g., the valve) are adapted so that, in a period of transition in either direction between delivery of pressure support to the user and delivery of a sub-therapeutic supply to the user, user breathing does not trigger repeated cycling between the first mode and the second mode of the flow diversion device 250. Accordingly, the valve 250 does not flutter to any significant degree at this transition.

Preferably, the flow diversion device 250 switches from the first mode to the second mode and from the second mode to the first mode according to the prevailing flow and pressure conditions. Typically, these flow and pressure conditions are generated by the gases supply device 200 and user breathing. Thus, the gases supply device 200 provides a base condition (e.g., flow and/or pressure) and the user breathing superimposes a transient variation in flow and/or pressure as the user inhalation and exhalation flow is superimposed on the flow from the gas supply device 200.

The flow diversion device 250 preferably has no means of control other than the prevailing flow and/or pressure conditions acting on the valve 250 and an associated valve member. The valve 250 is not actively controlled except by the flow generator 200 varying the prevailing pressure and/or flow conditions.

When the system gradually moves between a sub-therapeutic pressure and a therapeutic support pressure in the gases supply, the flow diversion device 250 closes to be in the second mode. Similarly, in moving from a therapeutic support pressure to a sub-therapeutic level, the flow diversion device 250 opens to be in the first mode.

The transition can be unstable for regular pressure or speed control flow generators. In particular, as the conditions reach a level at which the valve 250 will move from the first mode to the second mode, the fluctuation in conditions caused by user breathing can lead to the valve 250 opening and closing with each user breath. A similar effect can be noted where the pressure support is decreasing toward the sub-therapeutic level and approaches the transition conditions for the flow diversion device 250.

Accordingly, the flow diversion device 250 in the illustrated system switches from the first mode (i.e., the open mode) to the second mode (i.e., the closed mode) at a first set of conditions, and from the second mode (i.e., the closed mode) to the first mode (i.e., the open mode) under a second set of conditions. The first set of conditions is relatively higher than the second set of conditions. Accordingly, with the average pressure and/or flow increasing, when the flow diversion device 250 switches from the first mode to the second mode, the minimum pressure and/or flow is already above the pressure and/or flow at which it would switch from the second mode to the first mode. Similarly, when the average pressure and/or flow is decreasing, once the flow diversion device 250 switches from the second mode to the first mode, the minimum pressure and/or flow is already below the pressure and/or flow at which it would switch from the first mode to the second mode.

Preferably, the difference in the level of the conditions is greater than the fluctuation in the conditions resulting merely from user breathing. The fluctuation depends on system conditions. For example, pressure fluctuation in the region of the valve 250 depends on resistance to flow exiting the system. With the flow diversion device 250 open, the interior of the user interface 204 and flow diversion device 250 are more openly connected to the surrounding ambient conditions and the fluctuating pressure creates a smaller pressure swing than with the flow diversion device 250 closed. Furthermore, with a large bias vent 206, the pressure swing caused by breathing is reduced.

Certain characteristics of the gas supply apparatus 200 can exacerbate the pressure swing from user breathing. For example, a pressure feedback control operating to control the output of the flow generator can exaggerate the fluctuation in flow.

The valve 250 is biased toward the open condition. In the sub-therapeutic mode, the delivered supply is intended to allow the valve 250 to remain in the open condition. The pressure feedback control can have an adverse impact as the delivered supply approaches the condition that, in a steady state, would trigger the valve 250 to switch to the closed condition. In particular, within each breath cycle, the pressure control increases the output of the flow generator during inhalation relative to exhalation. This brings the flow passing the valve 250 to a critical point, thereby priming the valve 250 for closure. During the next expiration by the user, pressure rapidly increases in the circuit 202 and the "primed" or partially closed valve 250 now fully closes.

In some embodiments, the gas supply device 200 operates with a control method that reduces the occurrence of valve instability (i.e., valve flutter) caused by the fluctuation of the flow from user breathing. In particular, the control method for the gas supply device 200, at least as the supply condition approaches the transition conditions between the first mode and the second mode, is adapted to not significantly exacerbate, and preferably to alleviate, fluctuation in the particular system conditions that cause switching of the valve 250. For example, the valve 250, which will be described later, is sensitive to flow. In particular, the valve 250 is sensitive to flow from the gas supply device 200 to the user interface 204, to flow to ambient through the valve 250, or both. As the supply conditions approach levels where the valve 250 might be unstable, the control method controls the output of the gas supply device 200 according to an assessed average supply flow and a desired average flow. For example, the control of the gas supply 200 can implement a feedback control based upon average gases flow. Preferably, during this period, the method does not include a feedback control based upon pressure. This stabilises the flow, or at least removes a destabilizing influence on the flow delivered by the flow generator or gas supply device 200. The flow still fluctuates with user breathing, but the controller does not take steps that exaggerate this fluctuation.

Accordingly, in some embodiments, the control results in a substantially constant low flow generator speed and does not respond to user breathing by changing the speed of the flow generator during the breathing cycle. Because the flow is low and does not increase as much when the user inspires as it would for a pressure feedback control, the valve 250 is not "primed" for closure, and thus does not close during expiration.

In therapeutic CPAP mode (e.g., at circuit pressures above a low threshold of about 2-3 cm H2O), the controller provides feedback to the flow generator to maintain a "pressure control." During inspiration, this causes an increase in the delivered flow in order to maintain pressure, which brings the flow passing the valve 250 to a level that primes the valve 250 for closure. During the next expiration by the user, pressure rapidly increases in the circuit 202 and the "primed" or partially closed valve 250 now fully closes. Furthermore, the valve 250 is subsequently kept closed by the now continuous positive pressure (e.g., CPAP).

In effect, the above described two modes result from tuning the CPAP flow generator response to the oscillatory nature of a user's breathing and from using the resulting interaction of the pressure and flow to switch the valve mode without actually actively interacting with the valve 250 with a separate controller.

A benefit of this tuning between pressure control and flow control of the gases supply device 200 and user breathing is that, when the flow generator is switched between modes, the valve state can be controlled with minimal change in either pressure or flow alone to the user at the time of the switch.

When arranged and configured in accordance with certain features, aspects and advantages of the present invention, the system provides a sub-therapeutic pressure at the beginning of the session or at times when the apparatus considers the user to be awake. As used herein, sub-therapeutic pressures include pressures below about 4 cm H2O, preferably below about 3 cm H2O and more preferably pressures below about 1.5 cm H2O and most preferably pressures about 1 cm H2O.

The sub-therapeutic mode may be selectable by a user, may be selectable by an overall control algorithm of the apparatus, or may be an automatic function at the beginning of every session of use of the apparatus. Once the user is asleep, or after an initial time-set period of sub-therapeutic delivery, the apparatus transitions and delivers a therapeutic pressure.

Preferably, sub-therapeutic pressure is provided to the user in conjunction with monitoring the flow delivered to the user. The controller of the apparatus monitors the flow delivered to the user and adjusts control of the flow generator to reduce the likelihood or eliminate flow rates that may be insufficient to provide proper flushing of the user interface. For example, the control may reduce the likelihood of the average flow rate falling below about 10 liters per minute, preferably reduces the likelihood of the average flow rate falling below about 12 liters per minute, most preferably reduces the likelihood of the average flow rate falling below about 15 liters per minute.

For a given user interface, a particular flow rate may be considered sufficient to provide appropriate flushing. Across most user interfaces presently available, an average flow rate of about 15 liters per minute is thought to be sufficient. Whatever the chosen flow rate, while in the sub-therapeutic mode, the apparatus preferably adjusts operation of the flow generator to maintain an average flow rate close to the chosen flow rate. For example, the controller may maintain the average flow within about 5 liters per minute of this amount, or most preferably within about 2 liters per minute of this amount.

By way of example, the controller of the apparatus may control the flow generator by controlling the power input to the flow generator. In this case, in the sub-therapeutic mode, the controller may decrease power input to the flow generator when the measured average flow exceeds the desired flow range and may increase flow generator power when the average flow is below the desired range.

Alternatively or in addition, the controller may control some other parameter of the flow generator, such as, for example but without limitation, motor speed. In such a case, the controller may command an increase in motor speed if the flow is below the desired range and command a decrease in motor speed if the flow is above the desired range.

Alternatively or in addition, the flow generator may include a pressure source and a pressure regulator. In such a case, the controller may reduce the set pressure of the pressure regulator when the measured flow is above the desired range and may increase the set pressure of the pressure regulator when the flow is below the desired range.

Advantageously, the apparatus may operate in the sub-therapeutic delivery mode during periods where the user is awake but in a therapeutic delivery mode when the user is asleep.

Accordingly, the controller may provide an initial period of operation in the sub-therapeutic mode during each session of use. This feature may also be used in an apparatus that includes functions for determining that a user is awake during periods within the session. For example, the Fisher & Paykel Healthcare HC250 device with "Sensawake" function determines instances of user arousal and reduces the delivered pressure to a pre-set awake pressure once it determines that the user may be awake. By implementing the above-described controls in such a device, the device could, after reaching the awake pressure, enter the sub-therapeutic mode.

In the sub-therapeutic mode, the control aims to maintain a substantially steady flow at a flow level that is selected to be sufficient to maintain appropriate flushing of the user interface 204. As used herein, substantially steady flow means that the average flow over a period of multiple breaths (e.g., about 20 breaths) remains substantially constant or within a limited range (e.g., a range of up to about 5 liters per minute) despite changing system conditions. Changing system conditions includes, for example but without limitation, changing leak conditions due to changes in the efficiency of sealing of the user interface. By way of clarification and comparison, changes in system conditions that would see an increase in flow under a constant pressure controlled system of greater than about 5 liters per minute are responded to with a substantially steady flow in the sub-therapeutic mode.

In the therapeutic mode, the controller delivers a substantially steady pressure. This may include a pressure feedback control, or be the result of a flow generator with a steady pressure output for a given operating speed. Like substantially steady flow, substantially steady pressure refers to the average pressure over multiple breaths.

One non-limiting example control method that is arranged and configured in accordance with certain features, aspects and advantages of the present invention is illustrated in FIG. 1. The illustrated control method may be incorporated into an apparatus that is arranged and configured in accordance with certain features, aspects and advantages of the present invention. The illustrated method for implementing the sub-therapeutic mode commences at 100 and may be triggered by a conscious user choice, such as, for example but without limitation, by selecting a control mode using the electrical user control interface. In some embodiments, the mode may be an initial starting mode for the apparatus or may be commenced by the apparatus according to a wider control strategy.

After starting, a control command issues to the flow generator to cause the flow generator to operate at an initial level. See 102. For example but without limitation, the controller can supply a command motor speed as an input to the flow generator and a motor of the flow generator can be speed-controlled to the command motor speed. In some applications, the apparatus may provide one or more of one or more command pressure values, one or more command flow values or one or more motor power inputs as input parameters. Preferably, the initial command input parameter for the flow generator is at a level that would usually provide a sub-therapeutic pressure between about 0.2 cm H2O and 2 cm H2O with a user interface correctly fitted. In the illustrated example, the motor speed is set to about 4000 rpm.

An evaluation then is made regarding whether the user is asleep. See 104. Preferably, the controller maintains a value representing the controller's belief that the user is asleep or awake. This value may be a probability assessed by the controller of whether the user is asleep or awake. The value can be assessed against criteria to decide whether to proceed on the basis that the user is asleep or to proceed on the basis that the user is awake. The value may be maintained by, for example but without limitation, assessing recent breathing patterns of the user, assessing recent history of apneaic events and/or obstructed breathing of the user. This may be examined over a time period, such as, for example but without limitation, the preceding few minutes, ten minutes or other similar time period. Any suitable methods of making a determination that the user is asleep or is awake can be used. Some suitable methods are described in other patent publications, for example U.S. Pat. No. 6,988,994 and US 2008/0092894, which are hereby incorporated by reference in their entirety.

The "asleep" assessments, and the maintenance of a sleeping value, may be made according to a separate control program running in parallel with the control program described with reference to FIG. 1. The separate control programs may be generally separate subroutine routines that may be executed sequentially in a given execution cycle but also may operate in parallel. If a separate control program is used, the control program of FIG. 1 will determine whether the user is asleep or awake based on an input parameter maintained or output by the other control program.

If the program determines that the user is asleep, then a therapeutic pressure is applied. See 106. The application of therapeutic pressure application may begin, for example, by immediately proceeding to a predetermined starting point pressure (e.g., about 3 or 4 cm H2O or greater) for therapy. This pressure may be a preset of the device or may be a variable pressure set by a physician. In some configurations, the method may proceed directly to a full treatment pressure, for example, a treatment pressure prescribed by a physician and preconfigured in the device. In some configurations, the control method may proceed to an automatic titrating mode that commences at a starting therapeutic pressure and that adjusts the supply pressure according to breathing events, such as apneas, hypopneas, flow obstructions, and periods of normal breathing.

In the therapeutic mode, the control method preferably seeks to maintain a substantially steady pressure. For example, the controller may control the flow generator based on input from a pressure sensor that senses pressure in the user interface 204 using feedback from the pressure sensor to control the speed of, or power input to, the flow generator, or to control the input parameter of a pressure regulator. The pressure in the patent interface 204 can be sensed in any suitable manner. For example, the pressure can be sensed either by a sensor that is positioned directly in the user interface 204 or by a sensor that interfaces with a part of the flow path to the user interface 204 that is downstream of the flow generator.

In some embodiments, the substantially steady pressure can be generated using a fan having a substantially constant pressure output for a given fan speed across a wide range of flow or from a pressure regulator, such as a self-regulating pressure regulator for example but without limitation, that may, for example but without limitation, use a mechanically operative feedback control to adjust the pressure output according to a particular input parameter.

The therapeutic mode (e.g., positive pressure, CPAP or autotitrating) may proceed according to any suitable treatment program and/or method. Control of the particular applied pressure in these methods may be by a separate control program or routine running in parallel or otherwise in conjunction with the control program described with reference to FIG. 1.

With reference again to FIG. 1, the illustrated control method begins looping to determine when a user awakens so that the machine can respond to the awakening of the user. See 108. For example, the control loop depends upon the output of the separate control loop that determines on a continuous basis an awakened state of the user.

As shown at 110, if the user is still asleep, the method continues to apply the therapeutic treatment pressure. See 106. The control loop 106, 108, 110 continues until it is determined that the user is awake. If it is determined that the user is awake, the method commences the sub-therapeutic mode. For example but without limitation, the sub-therapeutic mode can be commenced by changing the input parameter to the flow generator so that the flow generator provides gases at a sub-therapeutic pressure. See 102.

Once again, the method determines whether the user is awake. See 104. If the user is awake, the method proceeds to measure the flow. See 118. At 118, 120, 124, the measure of the flow is compared against a preferred flow range and, at 124, 128, the input parameter sent to the flow generator is adjusted accordingly. Preferably, the method checks (see 118) an assessed flow against a lower flow value. For example, the method checks whether the recent average flow (e.g., the average flow over the preceding 5 breaths, 10 breaths, 10 seconds, 30 seconds or a similar period) is less than a lower threshold (e.g., about 15 L/min).

The lower threshold may be a fixed predetermined value. For example, the value may be chosen to be suitable for all suitable user interfaces. In some embodiments, the lower threshold value may be a settable value, for example, so that it can be set according to a particular user interface used by the user. In some embodiments, the lower threshold value may be taken from a table of values based on a determined identity of the user interface or might be assessed for a particular interface in a test mode performed by the apparatus. In the simplest case, a fixed preset flow value, such as a lower limit flow value of about 15 liters per minute, is thought sufficient to provide a significant improvement in comfort over prior art apparatus without compromising safety.

If the assessed average flow is less than the lower threshold level, the control method adjusts the input parameter to the flow generator to increase the output of the flow generator. For example, the controller may increase a demand motor speed. See 124.

An additional check may be provided after determining that the average flow is below the lower control limit. See 122. The additional check determines whether the pressure has reached a therapeutic pressure level. While shown occurring after the lower control limit check (see 118), the pressure level check can occur at any suitable time. For example, in the illustrated method, the additional check may be conducted between the lower threshold level check and the output increase. See 122, 118, 124. Preferably, the method checks an assessed pressure in the user supply against a pressure threshold, for example but without limitation, 4 cm H2O. See 122. Where the flow is assessed below the lower limit at 118 and the pressure is assessed above the threshold at 122, the method preferably proceeds to leave the sub-therapeutic mode and switch control to the therapeutic mode, as discussed above with reference to 106.

The control method may also set a fault condition, for example at 126. The controller may provide an indication of the fault condition as an alert on the electrical user control interface of the device or record the fault condition in a session data log maintained by the device for later review by the user, physician or other interested party.

Where the control method increases the flow generator output at 124, this is, for example, by increasing the demand parameter for the flow generator. The increase may be a fixed predetermined incremental increase, an incremental increase that varies according to the present value of the parameter, or an incremental increase that varies according to the difference between the present value of the average flow and the desired flow range. For example but without limitation, the new input parameter (e.g., the new motor speed in a control motor speed embodiment) may be a function of the present motor speed, the present average flow value and a desired average flow value.

Alternatively, if the average flow value is above the minimum range value (see 118), the control method checks the average flow value against an upper flow value threshold for the range. See 120. Preferably, to maintain a low sub-therapeutic pressure, the flow range between the minimum value and maximum value is kept to a minimum. For example, the flow range may be about 5 liters per minute or less, preferably about 3 liters per minute or less, and most preferably about 2 liters per minute or less.

Alternatively, both upward and downward adjustment of the control parameter for the flow generator can be made based on a single desired average flow value. This is particularly suitable if an adjustment increment for the control parameter is a function of the difference between the present average flow value and the desired average flow value. In this method, the check against the upper flow value threshold (see 120) can be removed with the method proceeding directly from 118 to 128 in the case where the average flow value is not less than the desired flow value. This arrangement will lead to frequent adjustment of the motor input parameter, but if the frequent adjustments are small, they may not be significant. Similarly, a configuration can be used to does not have a lower flow threshold being used.

If the average flow is determined to be above the preferred range at 120 (or at 118 according to the modified method discussed above), then at 128 the control method decreases the input parameter to the flow generator. For example, the decrease may be a predetermined increment, or an increment variable according to the present average flow, the present value of the input parameter or the difference between the present average flow and the desired average flow range. The method then returns to 104. The method set forth at 104, 118, 124, 120 and 128 broadly constitute a feedback control controlling the output of the flow generator according to a desired flow rate (or desired flow rate range) and based on an assessed average flow rate value.

Figure 3A:
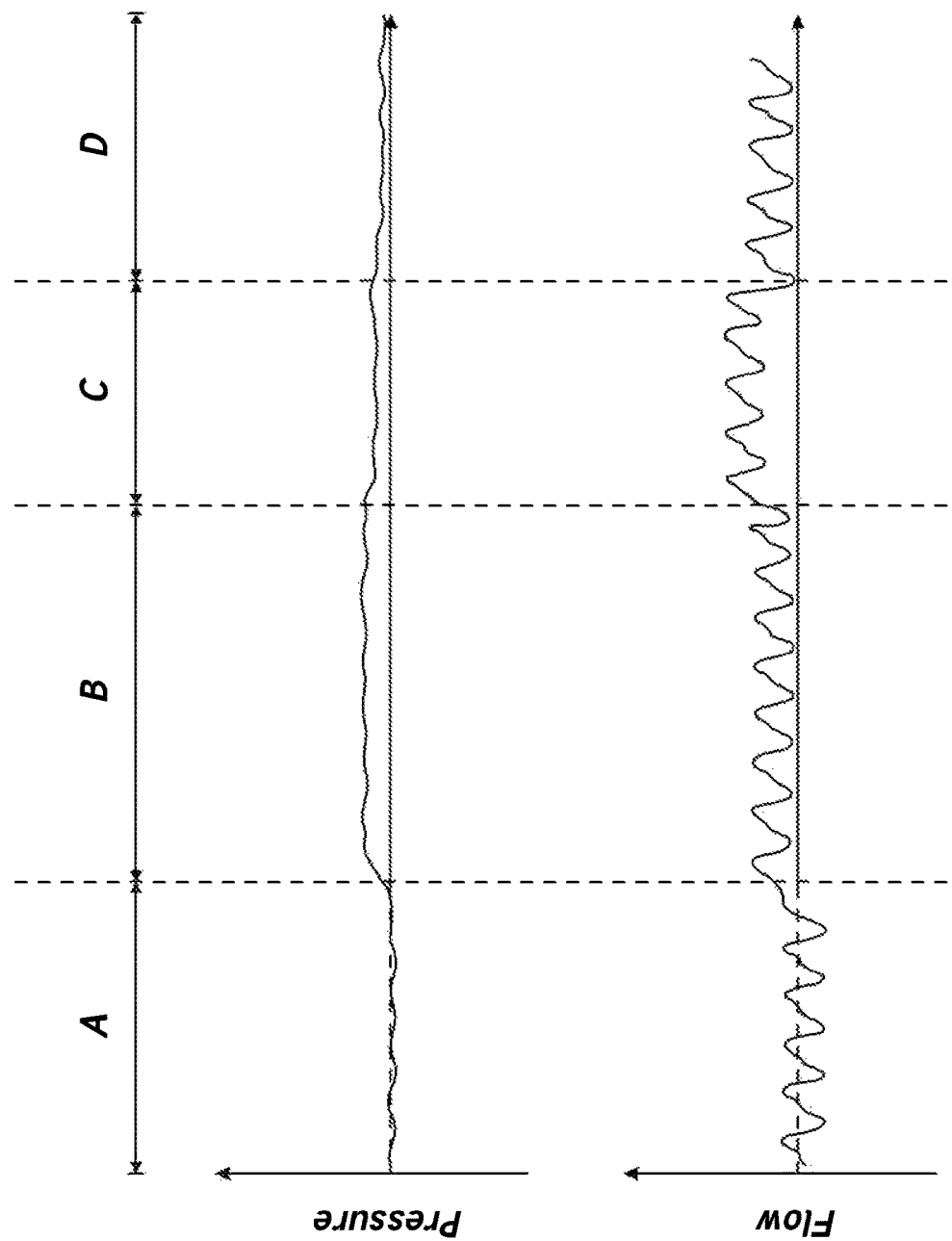
FIG. 3a and FIG. 3b are two non-limiting examples of plots of pressure and flow against time for portions of a session using an apparatus that is arranged and configured in accordance with certain features, aspects and advantages of the present invention.
Figure 3B:
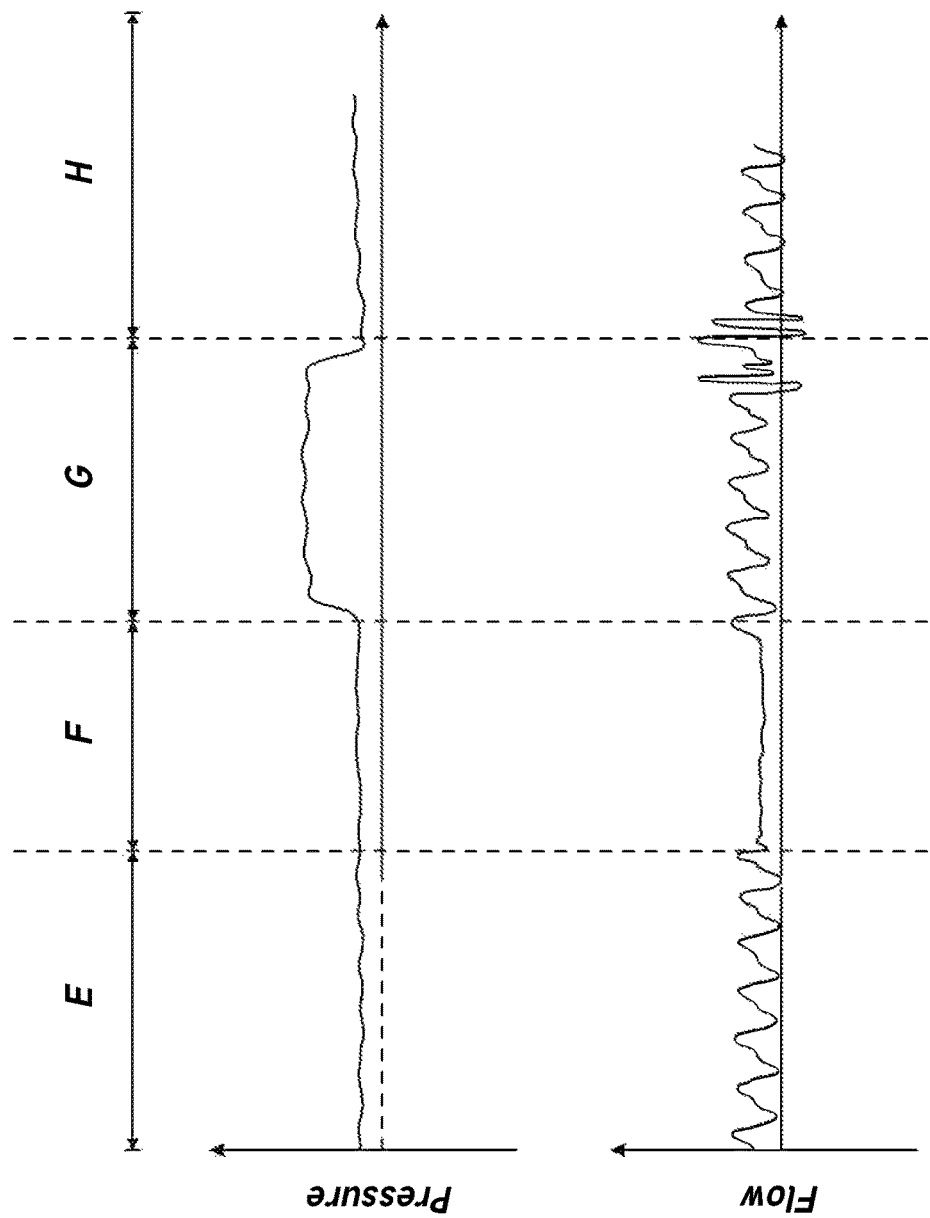

FIGS. 3A and 3B illustrate the effect of a control operating in accordance with certain features, aspects and advantages of the present invention. These plots are only intended to be representative and have been simplified accordingly. Section A of FIG. 3A shows normal breathing at the beginning of a session. The pressure is low (e.g., approximately 0 cm H2O) however the flow is averaging less than about 15 l/min.

Section B of FIG. 3A shows the device responding to the low flow rate in Section A, which results in increased flow generator speed (e.g., 118, 124 in FIG. 1), thereby causing the flow and pressure to rise.

Section C of FIG. 3A shows a leak being introduced (e.g., a mask leak occurs) and the level of flow increasing accordingly. The pressure drops slightly due to the leak.

Section D of FIG. 3A shows the algorithm responding to the increased level of flow by reducing the speed of the flow generator until the flow is again averaging approximately 15 l/min (e.g., 120, 128 in FIG. 1). The drop in speed further reduces the pressure.

Section E of FIG. 3B shows normal breathing.

Section F of FIG. 3B shows a user having an apnoea. The apnoea is shown by the flattening of the flow signal.

Section G of FIG. 3B shows that, in response to the event in Section F of FIG. 3B, the device raises the pressure and normal breathing resumes (e.g., 104, 106 in FIG. 1).

The chaotic flow signal at the end of Section G indicates that the user has awoken and, at Section H, the pressure is reduced accordingly until the approximately 15 l/min average flow is maintained again (e.g., 108, 102 in FIG. 1).

With reference again to FIG. 2, FIG. 2 presents a block diagram illustrating an embodiment of a breathing gases supply system that is arranged and configured in accordance with certain features, aspects and advantages of the present invention. The full system includes the gas supply device 200, which is an apparatus for delivering a supply of breathing gases, the supply conduit 202 and the user interface 204. As discussed above, the flow diversion device 250 can be located at, on or adjacent the user interface 204. Preferably, the flow diversion device 250 is in one of these locations because it allows venting to the atmosphere under certain operating conditions, which limits carbon dioxide rebreathing and provides oxygen. The supply conduit 202 extends from an outlet of the gases supply device 200 to the user interface 204.

The user interface preferably includes the bias flow vent 206 that allows a controlled leak from the user interface 204. The controlled leak allows the inside of the user interface 204 to be continuously flushed by fresh gases supplied by the supply device 200. The user interface 204 may comprise any of the many types of typical user interface for PAP delivery, including but not limited to, for example but without limitation, nasal masks, full face masks, oral masks, oral interfaces, nasal pillows, nasal seals or nasal cannulas.

The vent 206 may be located directly on the user interface 204, the vent 206 may be located adjacent the user interface 204 on a connector between the user interface 204 and the supply tube 202, or the vent 206 may be located through the wall of the supply tube 202 at a location close to the user interface 204, for example but without limitation.

The illustrated supply apparatus 200 includes a flow generator, which can comprise a fan 210 driven by an electric motor 212. Air is drawn through an inlet 214 in the housing of the apparatus by the fan 210. Pressurised air leaves the fan 210 and is supplied to the user through the supply conduit 202, for example. In some embodiments, controllable flow generators may draw on a source of high pressure gas and regulate a flow of gas from the high pressure source.

The apparatus 200 may include a humidifier 216. In some embodiments, the humidifier 216 comprises a pass-over humidifier where air passing through a humidifier chamber picks up a quantity of water vapour from a water supply contained in a reservoir 218. The water reservoir 218 may be heated by a heater 220. The humidifier 216 may be integrated within the same housing as the flow generator 210 or may be a separate component that can be used as an option.

The heater 220 and the motor 212 are supplied with power from a power supply 222. The amount of power to the motor 212 and the amount of power to the heater 220 can be controlled by outputs of a controller 224. The controller 224 is also supplied with power from the power supply 222. The controller 224 receives input from an electrical user control interface 226, for example but without limitation. The controller 224 preferably includes an embedded microcomputer with stored control programs or the like.

The controller 224 is also provided with an interface 228 that is used to connect with an external data source. For example but without limitation, the external data source may be a communication interface, such as a modem, or may be an interface to an external memory, such as a smart card, disk drive, flash memory or the like. For generic use, the interface 228 may be any suitable data communication port that is arranged and configured in accordance with any of the many available standards (e.g., a universal serial bus (USB)

port). The interface 228 can be used for connecting a wide range of peripheral devices. In some configurations, the interface 228 can be replaced by or augmented with a wireless communication device (e.g., Bluetooth, wifi, etc.).

The controller 224 preferably includes interfaces for receiving input from the electrical user control interface 226 and for receiving input from one or more sensors. The sensors can include a flow sensor 230 and a pressure sensor 232. The pressure sensor 232 can be positioned downstream of the fan 210. The flow sensor 230 can be positioned upstream or downstream of the fan 210.

The apparatus preferably is configured to perform control methods in the form of control programs executable by a microcomputer of the controller 224, for example but without limitation. In some embodiments, the controller 224 may comprise a fixed electronic circuit implementing control programs, a programmed logic circuit (e.g., an FPGA) implementing control programs or the like. Any suitable Electronic circuits and logic circuits implementing the control program may be used. In fact, all of the methods and processes described herein may be embodied in, and fully automated via, software code modules executed by one or more general purpose computers or processors. The code modules may be stored in any type of computer-readable medium or other computer storage device. Some or all of the methods may be embodied in specialized computer hardware. In addition, the components referred to herein may be implemented in hardware, software, firmware, or a combination thereof.

The illustrated apparatus, which preferably operates according to the control methods described herein, provides a sub-therapeutic mode of operation that is applied to the user while the user is awake. Breathing at this lower pressure may be less arduous than at the low therapeutic pressures applied at the commencement of therapy by other devices. This may be more comfortable and more pleasant for the end user, thereby improving therapy acceptance and compliance. At the same time, a minimum flow through the supply conduit 202 is provided to supply an adequate flow of fresh breathing gases to the interface 204 to flush the user interface 204 and reduce the likelihood of user re-breathing.

As described above, upon the detection of sleep, or a breathing disorder event, the apparatus will increase the delivered pressure to a predetermined or automatically determined therapeutic level at a comfortable and tolerable rate. When sleep or a breathing disorder event occurs, the user can be assumed to be asleep. Accordingly, the user should not be aware of or consciously experience the required higher therapeutic pressures, again thereby hopefully improving compliance.

Preferably, if the user wakes during the sleep session, the apparatus will revert to the sub-therapeutic state. The now conscious user will not experience, or will only experience for a limited time, the higher therapeutic pressures that are supplied while they are asleep because the apparatus returns to the sub-therapeutic state. This should also increase user compliance, particularly in the later stages of a sleep session, where otherwise the user may remove and cast aside the user interface before trying to return to sleep.

The method as described may be adapted by further variations. A few of these variations have been described above and several more will be described below. This is not an exhaustive summary and many further variations and alternatives are possible without departing from the scope of certain features, aspects and advantages of the present invention.

According to one variation, the apparatus may monitor one or more of the flow, the pressure, or other parameters that may indicate user respiratory rate. From the user respiratory rate, the controller may determine increased respiratory rate or increased breath volume. In the presence of increased respiratory rate or breath volume, or both, the controller 224 may increase the desired flow level in the sub-therapeutic mode. Increased respiratory rate or increased breath volume may be indicative of carbon dioxide rebreathing. Increasing the desired flow level in the sub-therapeutic mode may adapt the sub-therapeutic mode flow level to account for prevailing system conditions. The controller 224 may further filter this response according to the present user sleep state, which may help to reduce the likelihood of false positives due to dreaming, mask leaks and the like.

According to a further variation, one or more routines may be provided to check for occurrences of negative pressure in the user interface 204 during the sub-therapeutic supply mode. For example, the control program of the controller 224 may measure, derive or calculate a pressure in the mask or interface 204 on a continuous basis, or at least at a point in time or points in time during user inhalation. If the mask or interface pressure drops below a predetermined threshold (e.g., about 0 cm $H_2O$ or slightly below about 0 cm $H_2O$) during user inhalation, then the control program adapts the delivered therapy in an effort to reduce or eliminate these subzero pressures. These negative pressures may otherwise be experienced by the user as an undesirable feeling of being starved of air. The control program may apply the adaption instantaneously (e.g., applied within a breath cycle) or over a longer time period (e.g., adjusting an inhalation boost parameter periodically).

The controller 224 may obtain the pressure in the interface 204 by providing a sensor at the interface 204 to receive direct measurements of the internal pressure at the user interface. In some embodiments, the controller 224 may predict the pressure at the interface 204 from a measurement of the pressure of the delivered flow leaving the flow generator 210 (e.g., before or after the humidifier 216) and a predicted pressure drop between the location of the measurement and the interface 204 (e.g., across the length of the supply conduit). The control program can predict the pressure drop on the basis of the instantaneous flow along the conduit 202, for example. The control program can assume the conduit 202 has a certain flow resistance or can calculate the resistance of the conduit 202 or other assembly of components by implementing a pre-therapy test comparing delivered pressure and flow with no user interface connected to the conduit. The control program may implement any suitable method.

The control program may adapt the sub-therapeutic supply in a number of ways. One option would be to boost the target average flow. However, boosting the target average flow may boost the peak pressures during user exhalation and will boost the overall average pressure, thereby reducing some of the comfort advantages intended.

In some configurations, the controller can boost the supplied flow on user inhalation, for example, by increasing the output of the flow generator at the start of inhalation and subsequently reducing the output of the flow generator back to a lower level for exhalation. The control program may monitor user respiration to determine the start and end of inhalation by monitoring the variation in delivered flow or pressure on a breath-by-breath basis. While the average flow over multiple breaths is maintained substantially constant, the flow varies in an essentially sinusoidal manner in time with the user breathing. The flow is higher during inhalation than during exhalation. The control program can determine the inhalation phase from this variation.

According to another variation, the control program (e.g., the control program run by the controller) may provide a settable parameter providing for a boosted inhalation flow. For example, a settable parameter may be provided on a scale. A value of 0 indicates no boost to the input parameter for the flow generator during inhalation relative to exhalation. A progressively higher value indicates a progressively higher boost to the input parameter of the flow generator used during inhalation relative to exhalation. The user or the user's physician could set the parameter according to measurement, according to a qualitative assessment of total breathing volume of the user, or according to reported instances of breathlessness during the sub-therapeutic supply phase.

The controller 224, while implementing the sub-therapeutic phase, may control a baseline input parameter to the flow generator 210 according to the average delivered flow and, during periods of inhalation or periods of exhalation, may control the input parameter to the flow generator 210 according to a combination of the baseline parameter and the settable inhalation boost. According to this, the baseline could be applied during inhalation or exhalation. If the baseline is applied during exhalation, then the inhalation parameter is a boost above the baseline. Where the baseline is applied during inhalation, the exhalation pressure is a reduction below the baseline according to the set parameter. By boosting the flow (i.e., boosting beyond the normal fluctuation provided by the user breathing alone) during inhalation relative to exhalation, these variations reduce the likelihood of any feeling of starvation at the interface 204.

According to a further variation, the control method may include control of humidification of the breathing gases (e.g., by varying a power input to a humidification heater 220) such that humidification delivery in the sub-therapeutic mode is controlled independently of humidification delivery in therapeutic modes. For example, in the sub-therapeutic mode, the controller may reduce or disable humidification (e.g., by reducing or turning off power to the humidification heater 220).

According to a further variation, the apparatus may include a user selectable, or automatically initiated, test sequence. According to the test sequence, the control program causes the flow generator 210, 212 to deliver a controlled therapeutic pressure for a period of time. It is intended that the user will not consciously experience high pressures at the interface 204. The test sequence will provide an opportunity for the user to ensure that the mask is fitted correctly. The control program may provide for a test sequence selectable by a user at the electronic user control interface, or may provide for the test sequence to automatically commence at the beginning of the session, or both. The test sequence may provide for a pressure delivery at a preset minimum therapeutic pressure, a preset maximum therapeutic pressure, a preset test pressure, or another pressure selected according to previous use of the device (e.g., a 95th percentile pressure established from previous sessions).

In some configurations of the apparatus, such as described with reference to FIG. 2, the apparatus includes the flow sensor 230 and the pressure sensor 232. Each sensor, 230, 232 may be of any suitable type. For example, the flow sensor 230 may be a differential pressure sensor operating in conjunction with a flow restriction. In that case, parts of the differential pressure sensor may double as the pressure sensor. In some applications, an assessed pressure may be derived independently by a discreet pressure sensor. In some applications, the delivered pressure may be inferred from blower speed, or calculated from a sensed flow and blower speed, for example but without limitation. An assessment of the delivered pressure may also account for an estimated pressure drop between the PAP apparatus and the user, for example, by accounting for a pressure drop along the conduit 202 according to a measured flow. In addition, where the pressure sensor 232 is present, flow can be inferred from blower speed and the output of a pressure sensor rather than using a separate flow sensor. Otherwise, any suitable flow sensor can be used.

Figure 9A:
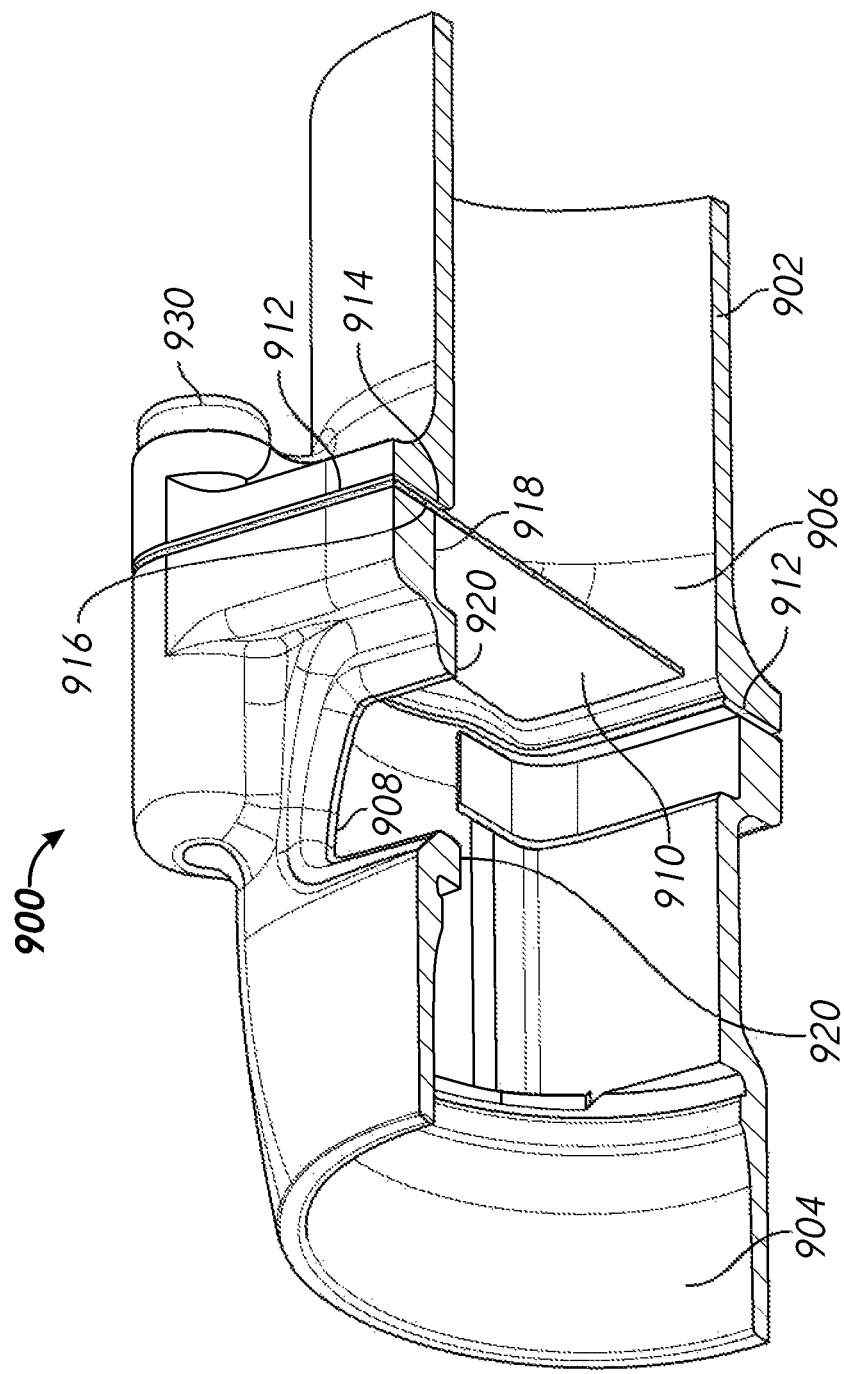
FIG. 9A is a cross-sectional side elevation of a flow diverting valve that is arranged and configured in accordance with certain features, aspects and advantages of the present invention.
Figure 9B:
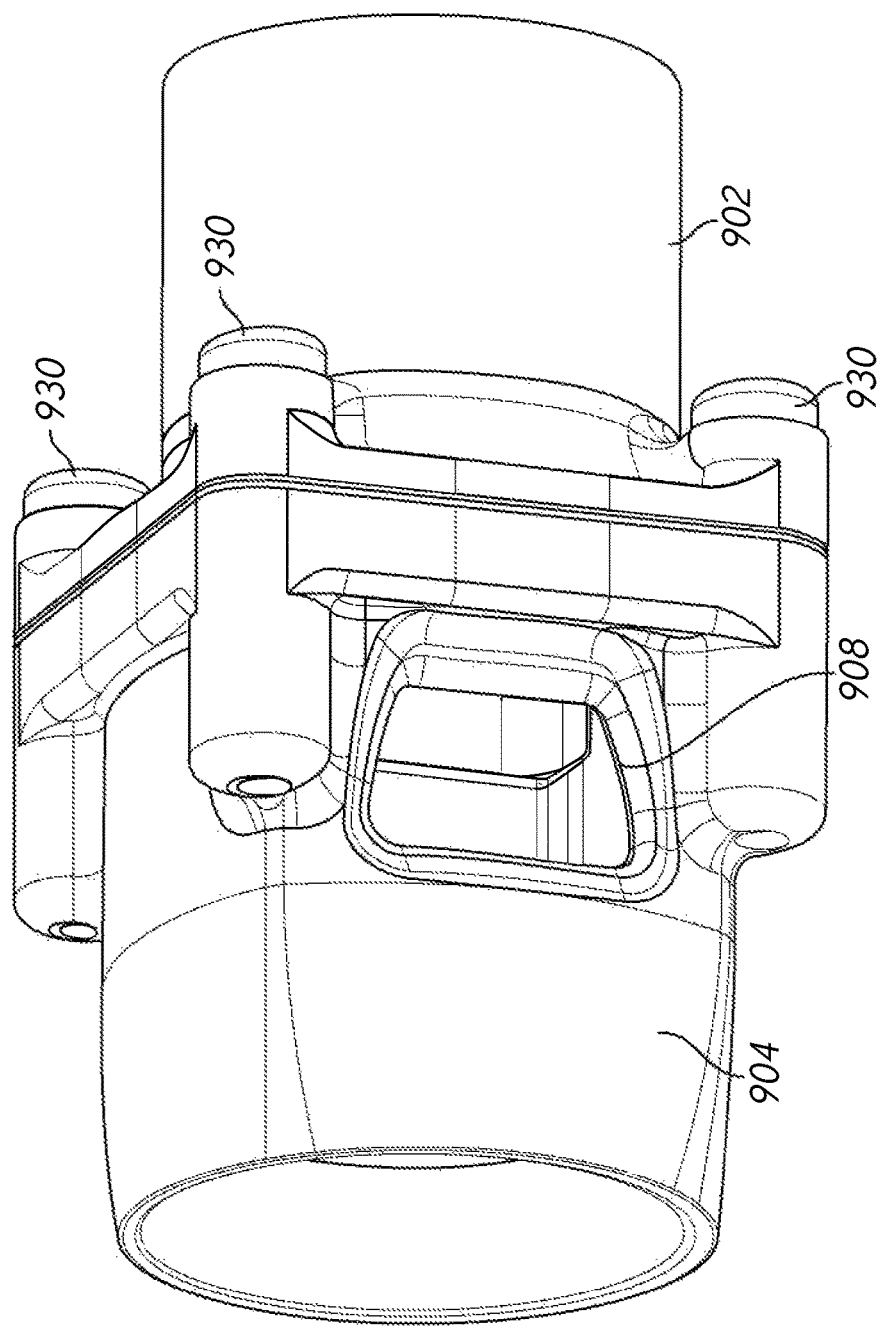
FIG. 9B is a perspective view of the valve of FIG. 9A.
Figure 9C:
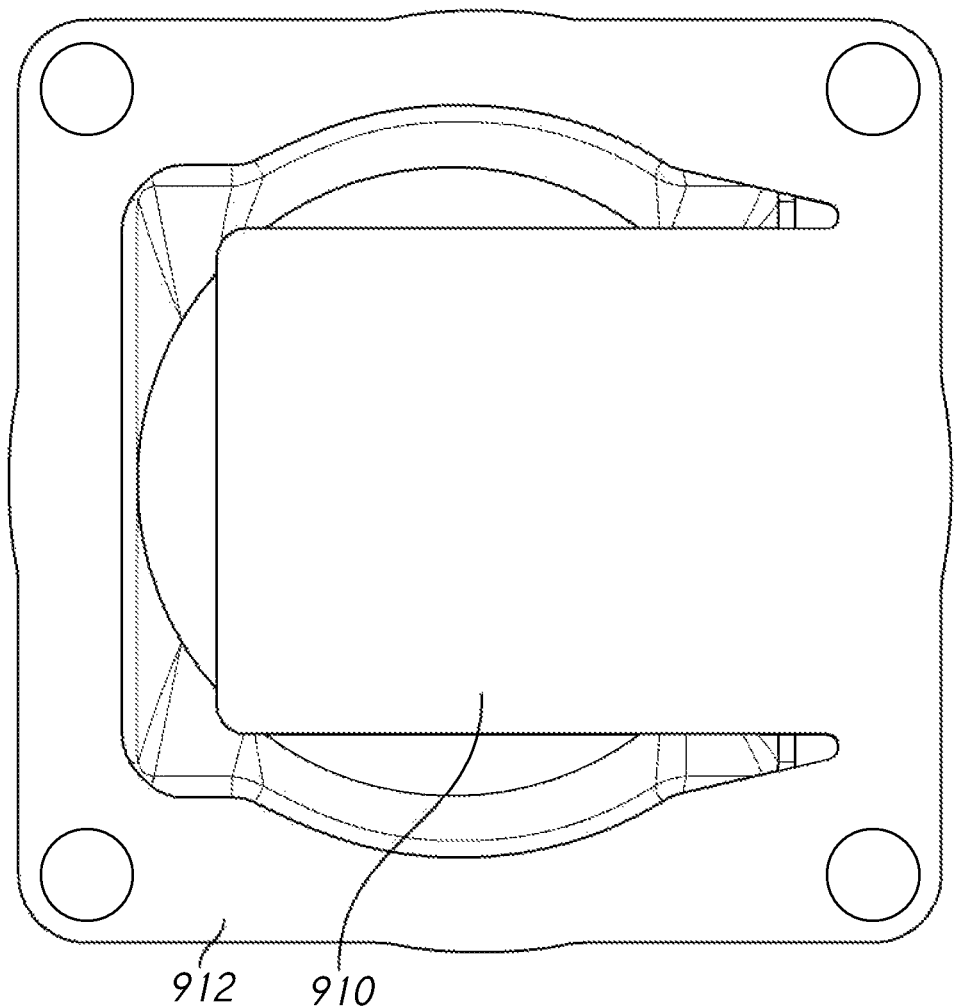
FIG. 9C is a cross-section of the value of FIG. 9A showing a profile of the valve.

FIG. 9A to FIG. 9C illustrate a flow diversion device 900 that can be used in an implementation of a system that is arranged and configured in accordance with certain features, aspects and advantages of the present invention. The flow diversion device 900 can be arranged as a connector for simplicity of assembly with other pre-existing components.

The illustrated flow diversion device 900 includes an inlet portion 902 and an outlet portion 904. In some embodiments, the inlet portion 902 comprises an inlet connector portion 902 and the outlet portion 904 comprises an outlet connector portion 904. The inlet connector portion 902 includes an external tapered connecting surface. The external tapered connecting surface can be a standard taper. The outlet connector portion 904 includes an internal tapered connecting surface. The internal tapered connecting surface is used to secure a swivel connector, for example but without limitation. Other configurations are possible.

A flow passage or bore is provided through a body of the flow diversion device 900 from the inlet end of the inlet portion 902 to the outlet end of the outlet portion 904. A central portion 906 comprises a flow port 908 extending through a wall of the flow diversion device 900. The flow path through the flow diversion device 900 can communicate with the ambient surroundings through the port 908.

A flexible valve member 910 extends into the flow path at a location between the inlet to the inlet portion 902 and the port 908. An internal perimeter surface 920 surrounding the port 908 may act as a land or valve seat for when the flow diversion device 900 is in the closed condition. In the closed condition, a valve flap cuts off flow from inside the user interface 204 to ambient surroundings through the port 908.

Flow through the flow diversion device 900 from the inlet of the inlet portion 902 to the outlet of the outlet portion 904 pushes against the valve member 910, which urges the valve member 910 toward the closed condition. Flow passing from the outlet portion 904 to the inlet portion 902 (e.g., in the case of user exhalation) pushes against the valve member 910 to urge it toward the inlet portion 902 and the opened condition.

The valve member 910 preferably is cantilevered from the inside surface of the wall forming the flow passage. The valve member 910 may be able to flex toward or away from the closed condition by bending adjacent its connection with the wall or by bending along its length. In some configurations, the valve member 910, when in the opened condition (i.e., extending into the flow path between the inlet and the outlet), the valve member 910 can bend toward the user during inhalation and/or toward the flow generator during exhalation. In the illustrated flow diversion device 900, the secured end of the valve member 910 is clamped between two portions of the flow diversion device 900. For example, a base of the valve member 910 may be clamped between an end surface 914 of the inlet portion 902 and an end surface 916 of the outlet portion 904.

With reference to FIG. 9C, the valve member 910 may be formed integrally with a gasket 912. The gasket 912 can be a perimeter gasket. In some configurations, the gasket 912 only extends a portion of the full perimeter of the flow diversion device 900. The gasket 912 may be sandwiched between the end surfaces 914, 916 around the circumference of the connector 900. In the illustrated configuration, the two parts containing the end surfaces 914, 916 of the flow diversion device 900 are secured together by a plurality of screws 930. In other configurations, the two portions of the flow diversion device 900 can be secured by snap fit connection, adhesives, over-moulding, ultrasonic welding or the like. In some applications, the valve flap 910 is a removable component.

Where the valve flap 910 displaces by bending along its length, the land or valve seat 920 for the port 908 preferably is disposed on or near a plane that is spaced away from the embedded portion of the valve member. In other words, the land or valve seat 920 is offset in a transverse direction of the illustrated passage such that, as the valve member 910 bends to cover the port 908, a portion of the valve member 910 toward the free end of the valve member 910 can sit against the land 920 and substantially close the outlet port 908. The offset advantageously allows the valve member 910 to easily cover at least a portion of the outlet port 908 by simply bending about one bending location. In some applications, the offset allows the valve member 910 to substantially cover the outlet port 908 without the valve member 910 having to adopt a convoluted shape.

In a simple arrangement, the offset is provided by a stepback or offset 918 displaced away from the land 920. Instead of the stepback 918, a curved surface may be provided between the base of the valve member 910 where it embeds in the wall of the flow diversion device 900 and the port 908. The curved surface may match the expected curvature of the valve member 910 when it is deflected by prevailing conditions to substantially cover the outlet port 908.

In some configurations, the flow passage cross-section in the region of the valve member 910 is a substantially square or rectangular cross-section and the valve member 910 comprises a matching but slightly smaller profile (e.g., square or rectangular shape). Preferably, a significant gap or space is provided between at least a portion of the perimeter of the valve member 910 and the inner surface of the wall defining the flow passage. The gap or space provides a significant flow path through the location of the valve 910 with the valve 910 in the open condition, as illustrated in FIG. 9A. By way of example, with reference to FIG. 9C, the overall flow passage of the illustrated valve can have a cross-sectional area of about 470 mm2. The valve flap can be about 16 mm wide and about 19 mm long such that it defines an area of about 300 mm2. Thus, the opening between the perimeter of the valve flap and the inner surface of the wall of the flow passage can be about 165 mm2. According to such a configuration, with the valve 910 in the open position, a substantial portion (e.g., slightly more than ⅓) of the flow path remains unimpinged by the valve. In some embodiments, the valve 910 may occlude about 50%, about 60%, about 70% or about 80% of the flow path. In other words, the valve 910 may occlude between about 50% and about 80% of the flow path. Preferably, the valve 910 may occlude between about 50% and 70% of the flow path. In some embodiments, the valve 910 may occlude between about 60% and about 80% of the flow path. In some embodiments, the valve 910 may occlude between about 60% and about 70% of the flow path. In some embodiments, the valve 910 may occlude about 65% of the flow path.

The preferred valve flap 910 is very flexible and can be formed as a single leaf of a suitable, flexible polymeric material. For example, the valve flap 910 in the illustrated valve can be made from LSR silicone with a Shore A hardness of about 40. The illustrated valve flap 910 can be moulded with a thickness of about 0.45 mm. The 0.45 mm thickness provides a sufficiently thin valve flap, wherein the valve flap 910 had a surface dimension of about 16 mm wide by about 19 mm long. Other sizes also can be used.

The valve port 908 is located downstream of the valve flap 910. The valve port 908 may be, for example, about 5 mm downstream to about 10 mm downstream, and preferably about 7 mm downstream, of the valve flap 910. The illustrated port 908 is approximately trapezoidal in perimeter shape, with the shorter of the two parallel sides being closer to the valve flap 910. In the illustrated embodiment shown in FIGS. 9A-9C, the port 908 has an area of about 86 mm2, a perimeter of about 36 mm2, an overall width of about 11 mm and an overall length of 8 mm. Thus, the area of the port 908 may be between about 10% and about 50% of the flow path, and most preferably between about 15% and about 25% of the area of the flow path.

Figure 10A:
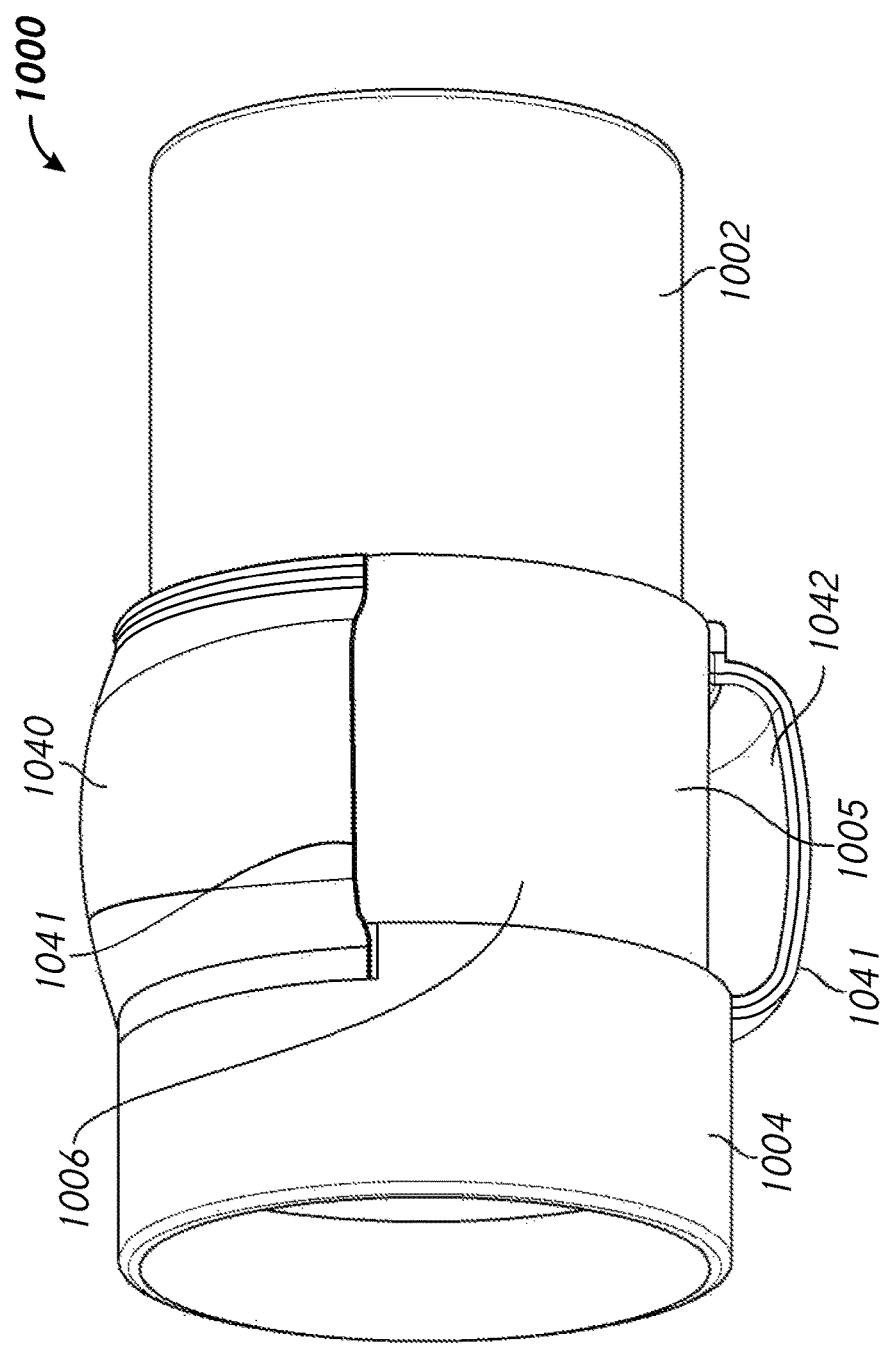
FIG. 10A is a side perspective view of a flow diverting valve that is arranged and configured in accordance with certain features, aspects and advantages of the present invention.
Figure 10B:
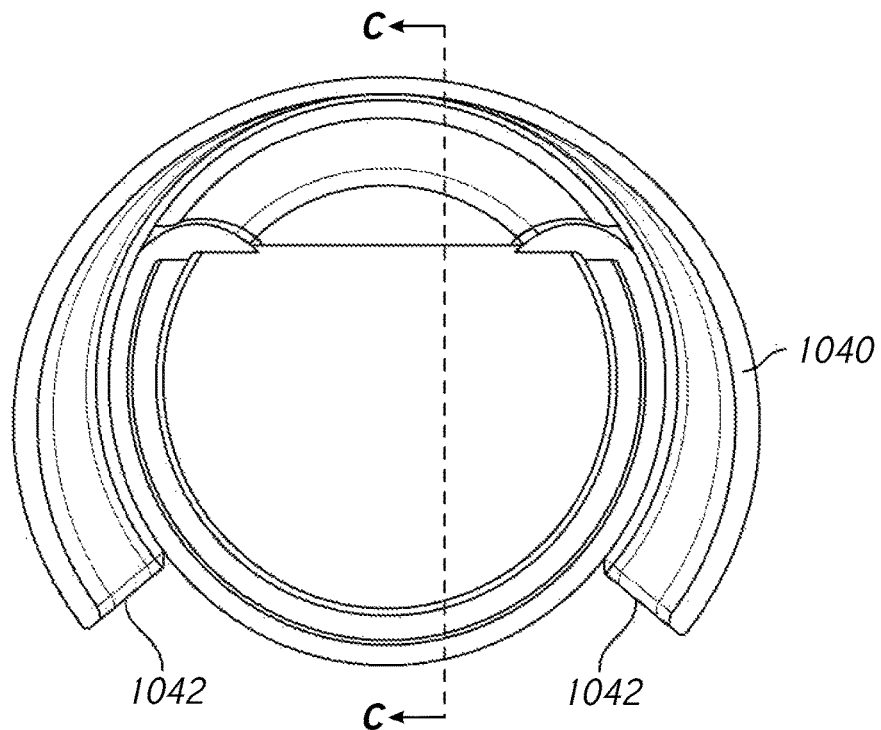
FIG. 10B is cross-sectional top view of the valve of FIG. 10A.
Figure 10C:
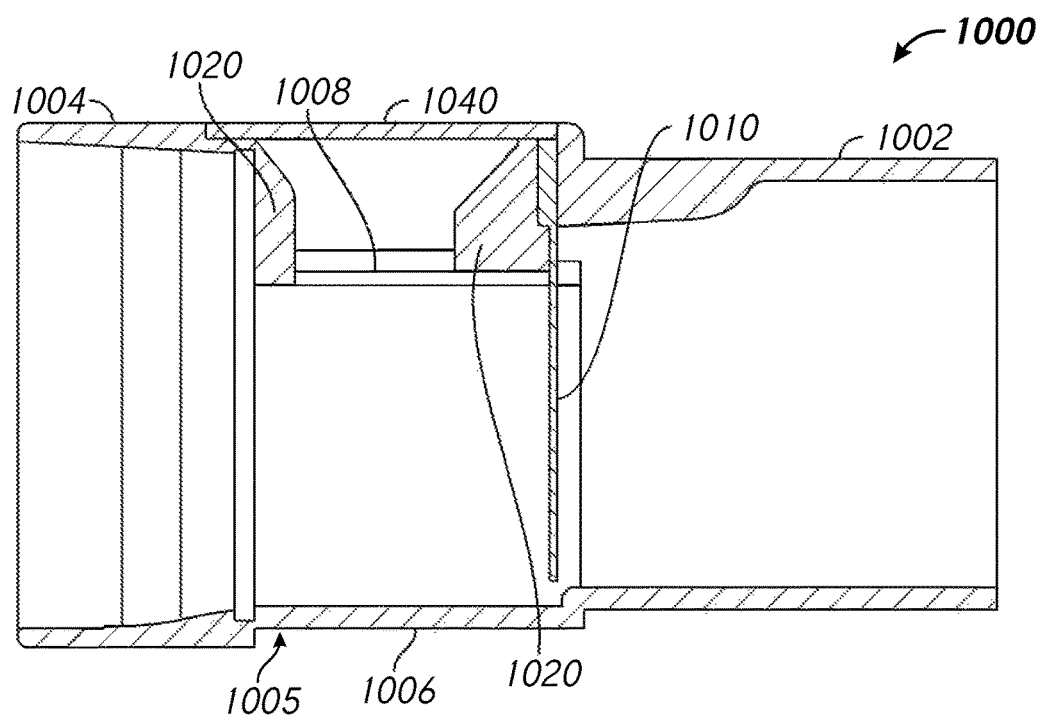
FIG. 10C is a sectioned view of the valve of FIG. 10A taken along the line C-C in FIG. 10B.
Figure 10D:
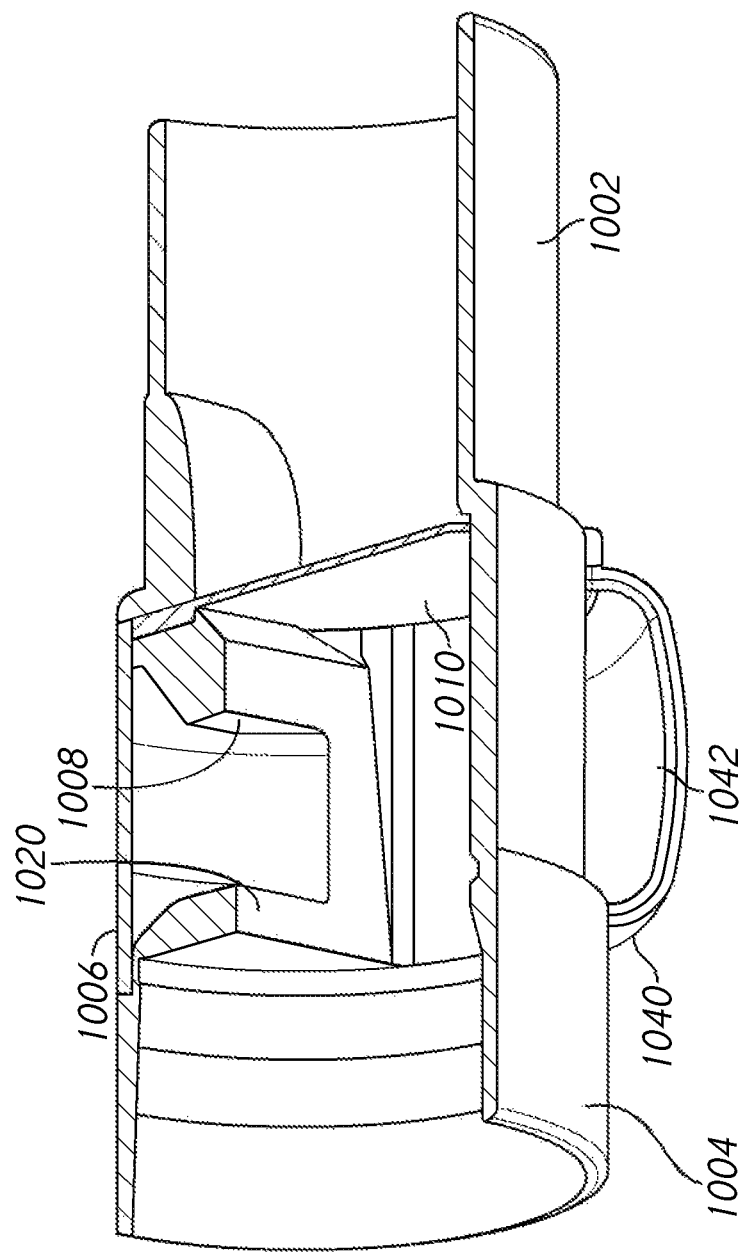
FIG. 10D is a perspective view of the sectioned valve of FIG. 10C.

With reference now to FIG. 10A to FIG. 10D, a further flow diversion device 1000 is illustrated. As illustrated in FIG. 10A, the flow diversion device comprises an inlet portion 1002 and an outlet portion 1004. The inlet and outlet portions 1002, 1004 can have any suitable configuration and can be configured similarly to the inlet and outlet portions 902, 904 described above.

A flow passage or bore is defined a body 1005 of the flow diversion device 1000 from the inlet portion 1002 to the outlet portion 1004. A central portion 1006 of the body 1005 comprises a flow port 1008 that extends through the wall of the body 1005 of the flow diversion device 1000. The flow path through the flow diversion device 1000 can communicate with the surroundings through the port 1008.

A flexible valve member 1010 extends into the flow path at a location between the inlet to the inlet portion 1002 and the port 1008. An inner surface 1020 surrounding the port 1008 may act as a land or valve seat for when the flow diversion device 1000 is in the closed condition. In the closed condition, the valve member 1010 generally cuts off flow from inside the user interface 204 to the ambient surroundings through the port 1008.

The port 1008, similar to the port 908, preferably is large enough to enable most of an exhalation flow to pass through the port 1008 into the ambient atmosphere. If the port 1008 is too small in area, the exhalation flow will take a path of least resistance around the port 1008 and go through the flow diversion device 1000 and the conduit instead. Because in such an instance, at least a large portion of the exhalation flow remains within the flow diversion device and the conduit, at least a portion of the exhalation flow likely would be rebreathed in the next inhalation. This is undesired.

On the other hand, if the port 1008 is too large in area, all of the exhaled gases will flow through the port 1008 to the ambient and there will be very little of the exhaled gases impinging upon the valve member 1010. The valve member 1010, when not positioned over the port 1008, creates a resistance to gases flow from the flow generator 210, 212. If the port 1008 is too large, the flow that urges the port 1008 into a resistance-generating position will be too small and will not be indicative of patient breathing.

Figure 11:
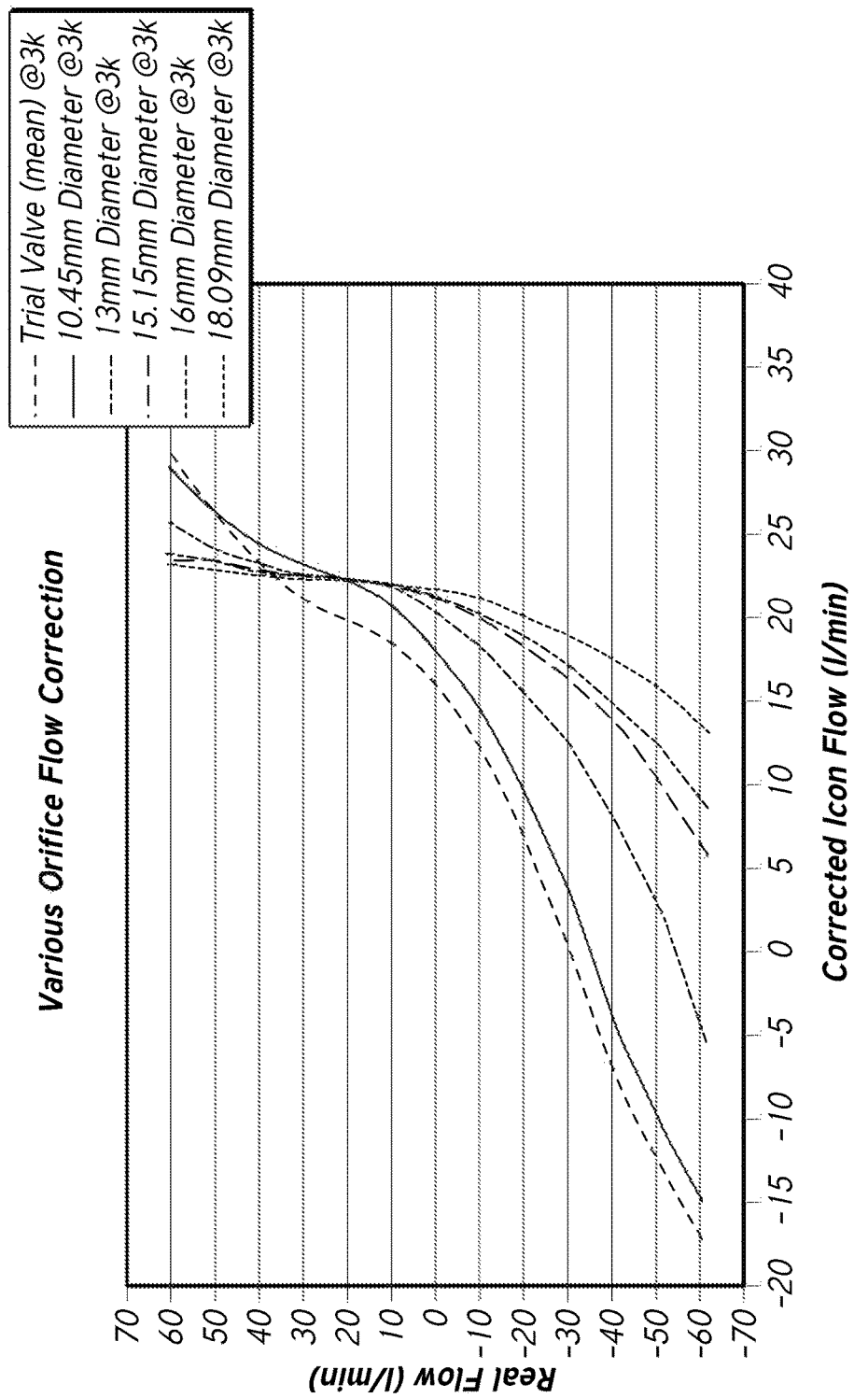
FIG. 11 is a graphical representation of an impact of valve orifice sizes on flow rates.

Under normal breathing conditions (e.g., a flow of about 25 L/min) and with a blower operating in a flow control mode with a flow rate of about 15-20 L/min, it has been found that the port 1008 preferably has a cross section of about 90 mm2. In some applications, the port 1008 can have a cross section of between about 40 mm2 and about 250 mm2. In some applications, the port 1008 can have a cross section of between about 85 mm2 and about 180 mm2. FIG. 11 represents various sizes of ports 1008 and the impact on flow rates.

With respect to the valve member 1010, for the valve member 1010 to function as a non-rebreathing valve, the size of the valve member 1010 preferably is large enough to substantially occlude the flow path from the outlet portion 1004 to the inlet portion 1002. If the valve member 1010 is too small, the exhalation flow will take the least resistance path and go down the conduit. If the exhalation flow goes down the conduit, then the exhalation flow likely will be rebreathed on the next inhalation.

With the valve member 1010 being generally perpendicular to the gases flow, the resistance to flow from the flow generator can be maximized. Thus, during exahation, a larger valve member 1010 can increase the resistance to flow from the flow generator. It currently is believed that information regarding a user's breathing can be amplified and the controller 224 thereby can receive data having a better resolution with a larger valve member when compared to a smaller valve member or with a valve member without a valve seat when compared to a valve member with a valve seat. The valve member 1010, however, desirably is small enough to allow substantially free movement of the valve member 1010. In the illustrated configuration, the valve member 1010 does not have a seat in the flow path from the flow generator to the interface.

In the illustrated configuration, the port 1008 is covered with a shroud 1040. The shroud 1040 extends around at least a portion of the outer surface of the body 1005. In some configurations, the body 1005 is generally cylindrical and the shroud 1040 extends around a portion of the circumference of the body 1005. In the illustrated configuration, the shroud 1040 extends around an outer surface of the central portion 1006 of the body 1005. The shroud 1040 has a first end and a second end 1041 that define openings 1042. Gases passing out of the port 1008 pass through a passage defined between the illustrated shroud 1040 and the central portion 1006 of the body 1005 and are exhausted to the ambient atmosphere through the openings 1042. Similarly, air can pass through that same passage, into the port 1008 and into the flow diversion device 900.

Other valve constructions also are possible without departing from the general scope of the present invention. In some configurations, valves can be used that are similar to those described in U.S. Provisional Patent Application No. 61/504,295, filed Jul. 4, 2011, which is hereby incorporated by reference in its entirety. In addition, the Quattro anti-asphyxia valve by ResMed has suitable characteristics, although not as good as the valve described with reference to FIG. 9A to 9C. Other valve constructions may be devised that meet the desired functional criteria for opening and closing with respect to the prevailing conditions in a stable manner. These preferred functional aspects will be apparent from the discussion below with reference to FIGS. 5, 6, 7 and 8.

Example Tests of Values and Systems

Behaviour of systems that have been arranged and configured in accordance with certain features, aspects and advantages of the present invention (e.g., utilising the valve described with reference to FIGS. 9A-9C and also an alternative commercially available valve) are described below. The tests demonstrated comparative performance of the valves and comparative performance of different control methods when used with the valves. Tests were conducted using a test setup as illustrated in FIG. 4.

Figure 4:
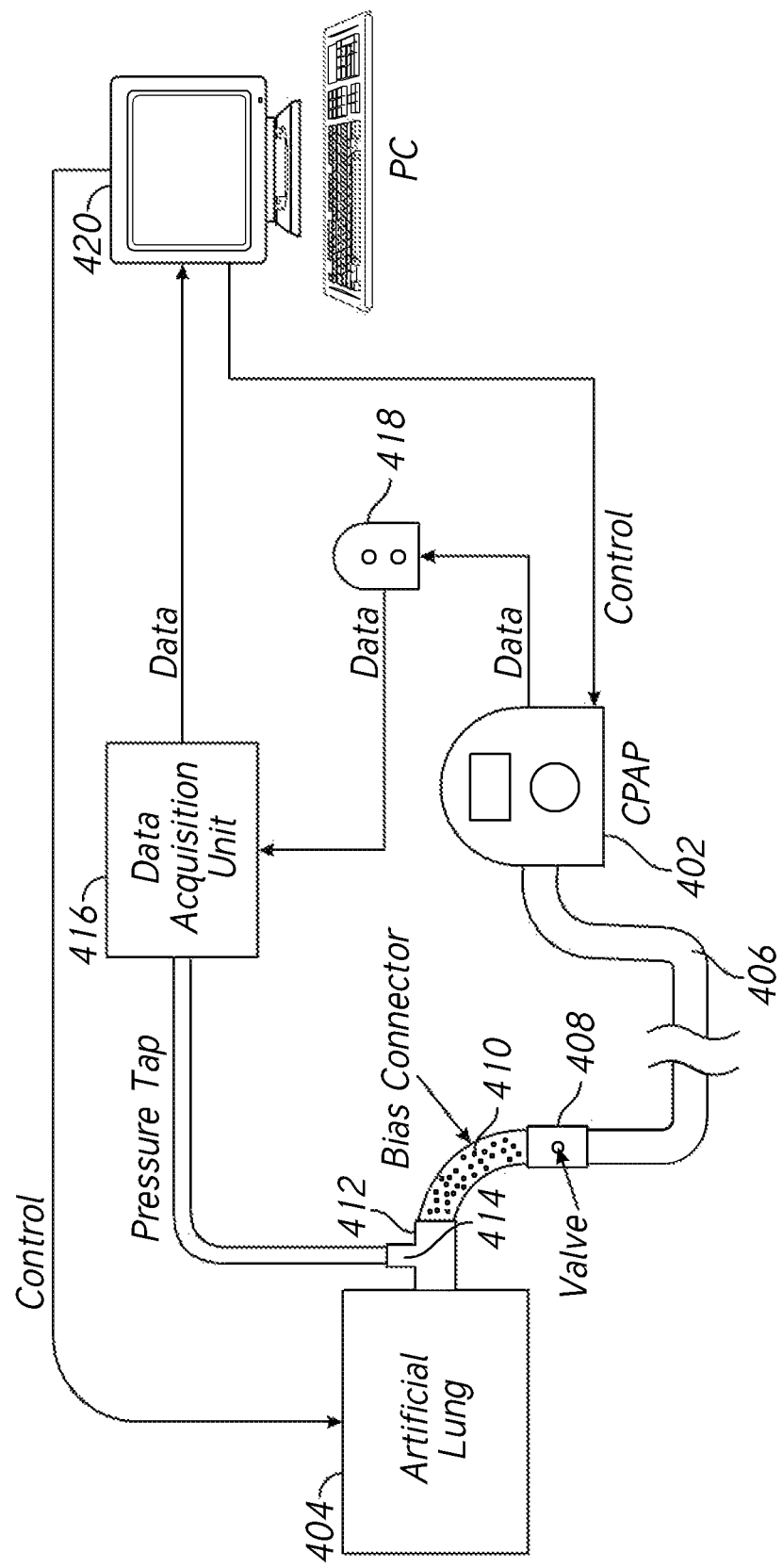
FIG. 4 is a block diagram of an experimental setup used to evaluate machines arranged and configured in accordance with certain features, aspects and advantages of the present invention.

The test setup illustrated in FIG. 4 comprises a CPAP flow generator 402 that is connected to deliver flow to an artificial lung 404. The CPAP flow generator 402 used in the experiments described herein was a Fisher & Paykel ICON Auto available from Fisher & Paykel Healthcare Limited, Auckland, New Zealand. The CPAP flow generator 402 featured modified software that was modified to remove lower limits. The artificial lung was an ASL5000 available from Ingmar Medical Ltd of Pittsburgh, USA.

The CPAP flow generator 402 was connected to the artificial lung 404 via a delivery conduit 406. The delivery conduit 406 was the 1.8 m supply hose supplied with the ICON Auto.

Between the user end of the delivery conduit 406 and the inlet port of the artificial lung were, in series, the valve 408 being tested, a bias flow connector 410, and a connector 412 including a port 414 for measuring characteristics of the gases stream. The bias flow connector 410 was an elbow from an HC407 nasal mask available from Fisher & Paykel Healthcare Limited. In the illustrated setup, the port 414 of the connector 412 was connected to a data acquisition unit 416 for measuring pressure at the entrance to the artificial lung. Additional data collected by the CPAP flow generator 402, including delivered flow, was supplied to a data interface box 418 and on to data acquisition unit 416. The collected data from data acquisition unit 416 was provided to a computer 420 or other suitable processing unit. The computer 420 can be connected to the artificial lung 404 to provide control signals to the artificial lung 404 and to the CPAP flow generator 402 to provide control signals to the CPAP flow generator 402.

Testing of Valve Characteristics Under Different Control Modes

In a first set of tests, the apparatus shown in FIG. 4 was used to consider the characteristics of the valve shown in FIGS. 9A-9C and the characteristics of an existing anti-asphyxia valve. These tests show both comparative performance of the valves and comparative performance of the control methods. The existing anti-asphyxia valve is supplied with the ResMed Quattro Full Face User Interface (available from ResMed Pty Limited of Sydney, Australia). The tests demonstrate some of the advantages of the preferred control (i.e., the control as used with either valve) and some of the advantages in this application of the valve of FIGS. 9A-9C over the ResMed anti-asphyxia valve.

For each valve, two series of tests were conducted. For each test in each series, the artificial lung was set up to run through a breath test sequence including: (1) four breaths at 250 ml tidal volume; (2) pause; (3) four breaths at 500 ml tidal volume; (4) pause; (5) four breaths at 750 ml tidal volume; (6) pause; (7) and four breaths at 1000 ml tidal volume. All breaths were sinusoidal at 15 breaths per minute with a 1:1 expiration to inspiration ratio.

In the first test series, the CPAP flow generator 402 was controlled to run at a constant motor speed for the duration of each test. That is, the device ran without pressure or flow feedback control. The device 402 was set to run at a speed at which the delivered average flow was expected to be low and the valve 408 open. The breath sequence was played and the behaviour of the valve 408 was noted. The speed was increased by 1000 rpm and the process was repeated. This cycle was continued, increasing the speed by 1000 rpm each time until the valve 408 reached a stable closed state. Then the process was repeated, reducing the speed by 1000 rpm in each of the test sequences until the valve 408 reached a stable open state. At each of the tests, the behaviour of the valve 408, the average mask pressure and the average flow rate were recorded.

Figure 5A:
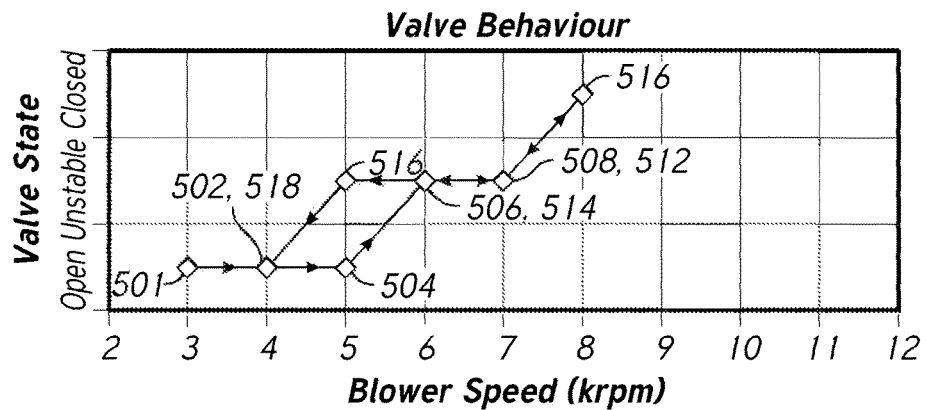
FIGS. 5A to 5F are plots that show opening and closing characteristics of a flow diversion device that is arranged and configured in accordance with certain features, aspects and advantages of the present invention.
Figure 5B:
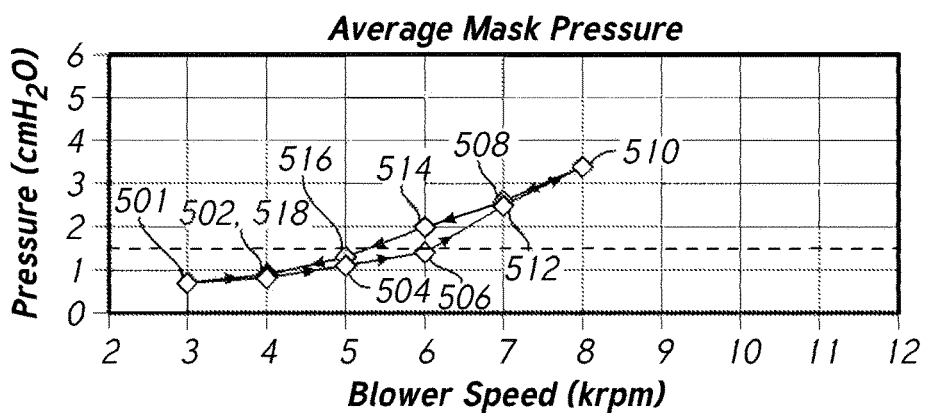
Figure 5C:
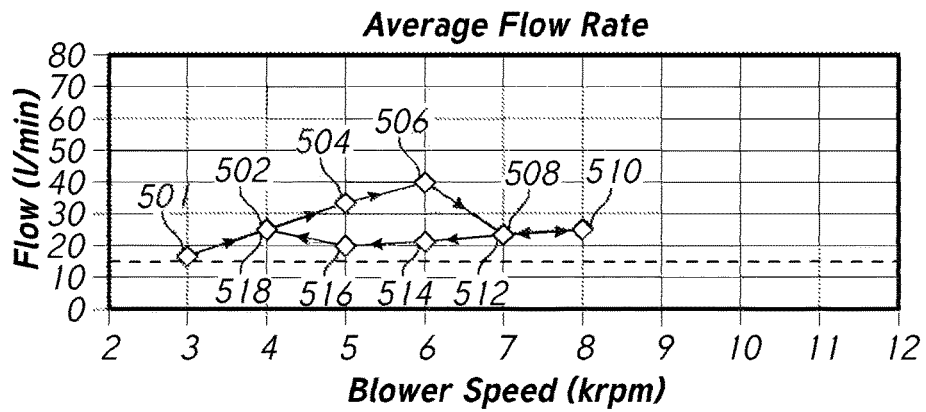
Figure 6A:
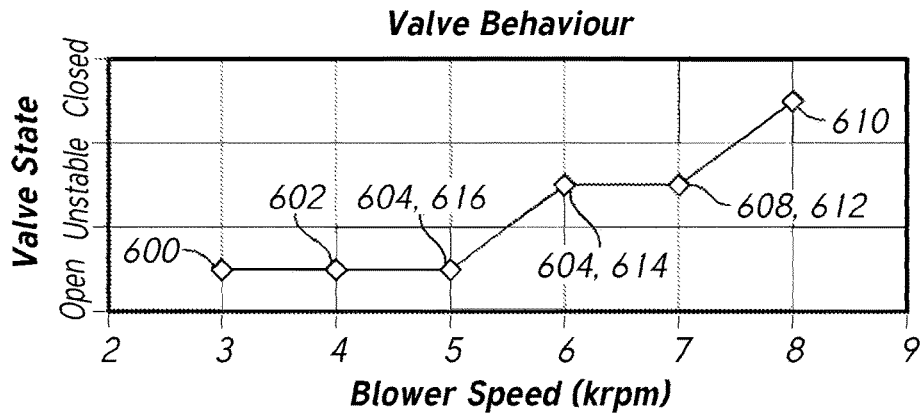
FIGS. 6A to 6F are plots that show opening and closing characteristics of a flow diversion device that is arranged and configured in accordance with certain features, aspects and advantages of the present invention.
Figure 6B:
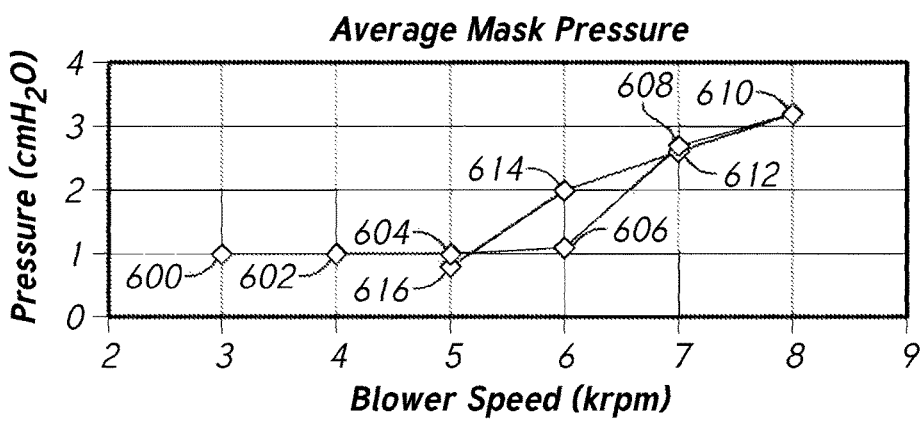
Figure 6C:
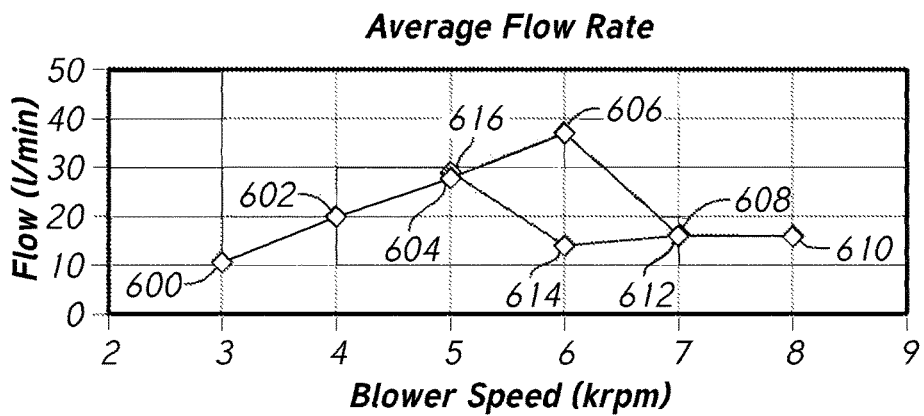

For the valve illustrated in FIGS. 9A-9C, the results of this sequence of tests are illustrated in FIGS. 5A-5C. These figures are discussed in more detail below. For the ResMed Quattro valve, the results of this sequence of tests is illustrated in FIGS. 6A-6C. These results are discussed in more detail below.

Figure 5D:
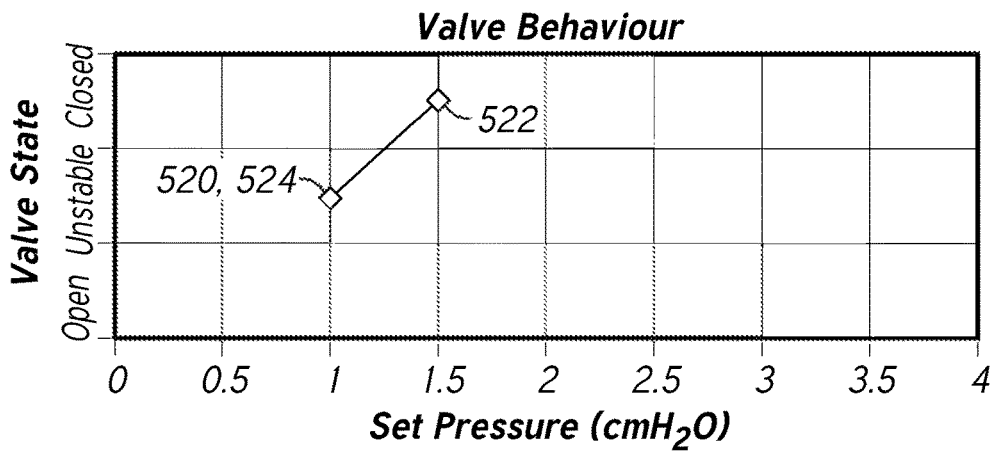
Figure 5E:
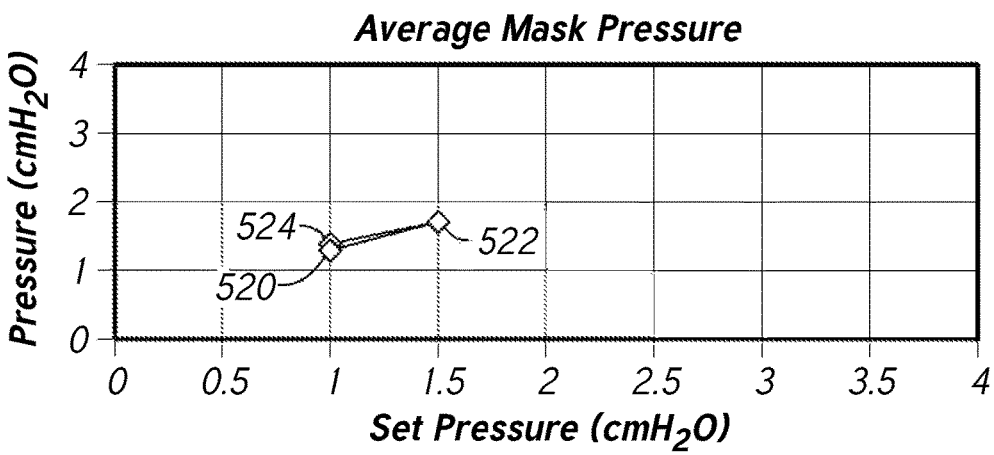
Figure 5F:
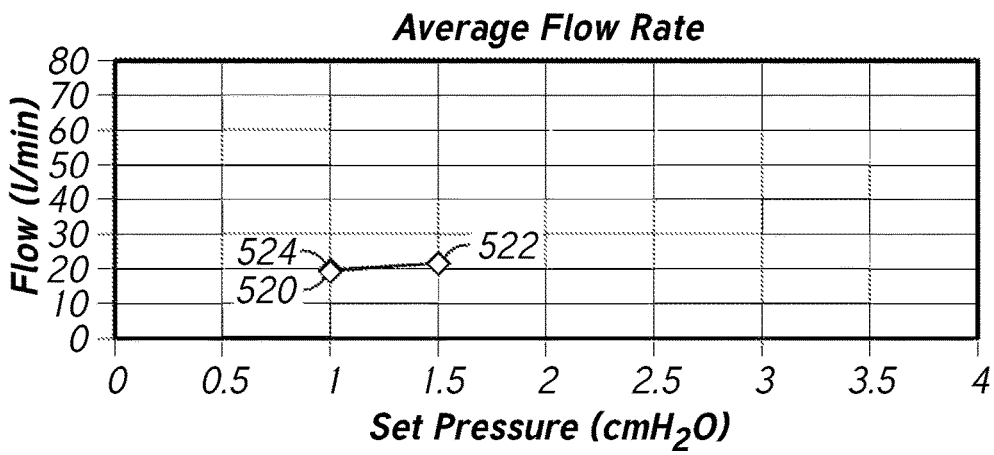
Figure 6D:
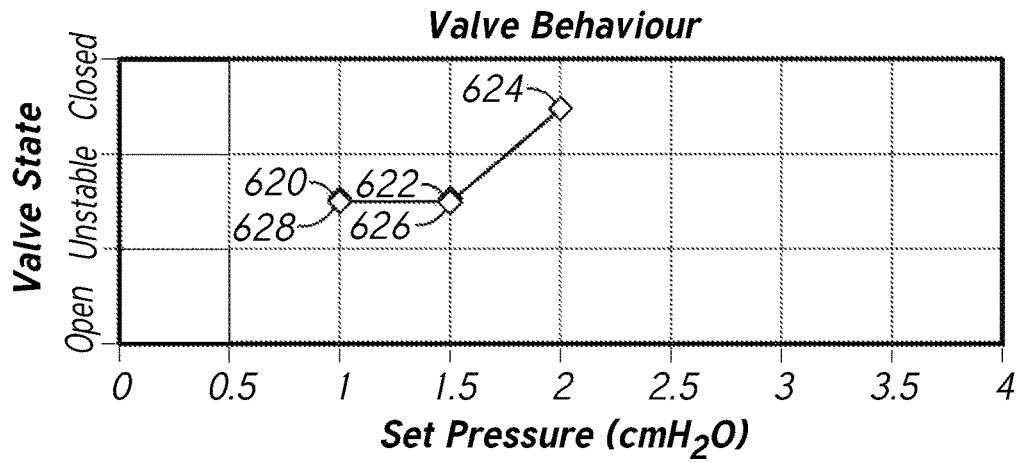
Figure 6E:
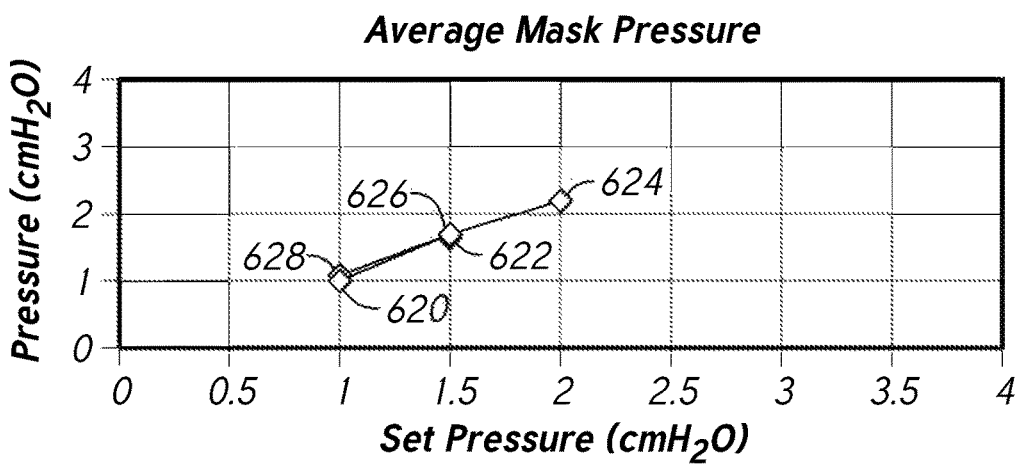
Figure 6F:
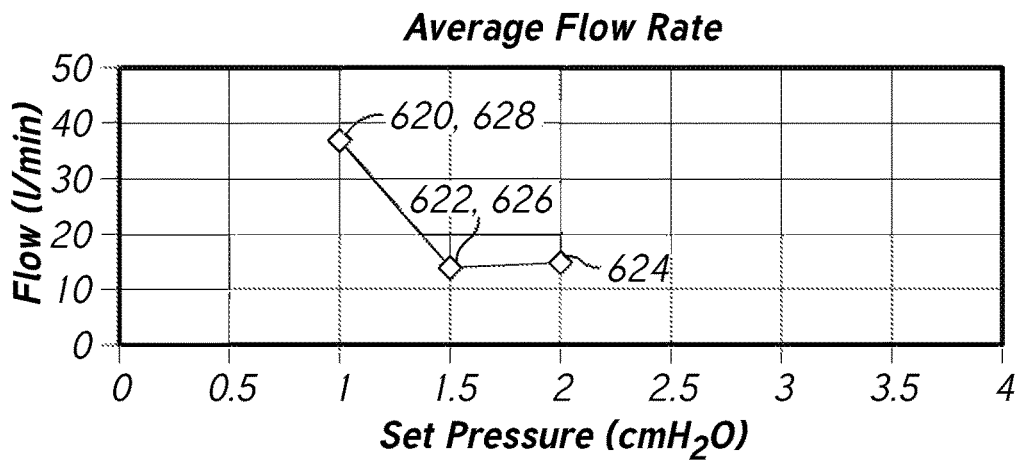

In the second sequence of tests on each valve 408, the CPAP flow generator 402 was run in a pressure feedback mode. The first test in the sequence had the set pressure for the flow generator at 1 cm H2O. Subsequent tests were conducted at increasing pressures, increasing the set pressure by 0.5 cm H2O for each subsequent test. Once the valve 408 reached a stable closed state, the process was repeated in reverse, reducing the set pressure by 0.5 cm H2O for each subsequent test. For each test, the state of the valve 408, the average flow and the average pressure were recorded. The results of this testing for the valve of FIGS. 9A-9C are illustrated in FIGS. 5D-5F. The results of this testing for the ResMed Quattro valve are illustrated in FIGS. 6D-6F.

Test Results for Valve of FIGS. 9A-9C

FIGS. 5A to 5C illustrate the behaviour of the valve 408 shown in FIGS. 9A-9C (i.e., the flow diversion device 900) under constant flow generator speed conditions. This illustrates, for example, the way the valve 408 will behave when the flow generator 402 is controlled with slow feedback based on average flow. The flow generator 402 will not react to the breathing cycle changes in flow or pressure and, over a sequence of breaths, will maintain essentially a constant flow generator speed. The instantaneous flow and pressure will fluctuate as the user breathes. FIG. 5B, which indicates the measured pressure, and FIG. 5C, which indicates the measured flow, both represent the average of the pressure or flow over the breaths of the test. The valve state behaviour in FIG. 5A was by observation. Either the valve 408 remained closed across all of the sequence of breaths, the valve 408 remained open across all of the sequence of breathes, or was instable and moved between the open and closed states in response to the breathing cycle.

The sequence of tests is indicated by the sequence of data points 501, 502, 504, 506, 508, 510, 512, 514, 516, 518. For simplicity, this sequence of data points is indicated by the same reference numerals in each of FIGS. 5A, 5B and 5C.

In FIG. 5A, it can be seen that the behaviour of the illustrated valve, when commencing in the open state, remains stable in the open state at blower speeds of 3000, 4000 and 5000 rpm (data points 501, 502 and 504 in FIG. 5A). At these blower speeds, the pressure delivered to the artificial lung remains below about 1.5 cm H2O (data points 501, 502 and 504 in FIG. 5B). Also within this range, the delivered flow at 3000 rpm was above about 15 liters per minute and the delivered flow at 5000 rpm above about 30 liters per minute. Accordingly, the illustrated valve provides for substantial adjustment of the delivered flow to compensate for large bias flow vents or leaks at the mask without excessively increasing the delivered sub-therapeutic pressure and with the valve staying stable in the open position.

With the illustrated valve of FIGS. 9A-9C and the illustrated flow generator, when reducing the output of the flow generator in response to user awakening, and subsequently entering the constant average flow (i.e., constant rotor speed) mode, the initial flow generator speed should be at or below 4000 rpm so that the valve exhibits the initial stable behaviour (see, for example, the transition between data points 516 and 518 in FIG. 5A).

FIGS. 5D-5F illustrate the results of testing in the pressure feedback mode. As discussed above, the pressure feedback mode is entered to provide therapeutic pressures once the user is asleep. One preferable characteristic of the valve illustrated in FIGS. 9A-9C is to exhibit stable closed behaviour under pressure feedback control at a set pressure that is close to the average mask pressure delivered immediately prior, when the valve behaviour was stable open under constant rotor speed control.

With reference to data points 520 and 524, the valve of FIGS. 9A-9C exhibits unstable behaviour with the pressure feedback control at 1 cm H2O set pressure whether commencing at this set pressure or returning to this set pressure from higher set pressure. However, as indicated by data point 522, at 1.5 cm H2O set pressure, the valve exhibits stable behaviour. At this set pressure, the system delivered an average pressure of about 1.7 cm H2O and delivered an average flow of about 20 liters per minute.

Performance of the Valve of FIGS. 9A-9C in Combination with Preferred Control Modes The delivered average mask pressure with the valve stable and closed (e.g., about 1.7 cm H2O) is less than about 1 cm H2O higher than the delivered average mask pressure under the constant rotor speed control with the valve stable open (data points 501, 502 and 504 in FIG. 5B). The delivered average flow at this setting is within the range of the delivered average flow indicated by data points 501, 502 and 504 in FIG. 5C.

Data point 522 relates to the valve stable and closed (i.e., pressure mode) and generates a mask pressure of about 1.7 cm H2O. Data point 518 relates to the valve stable and open (i.e., speed mode) and generates a mask pressure of about 0.9 cm H2O. The delivered average mask pressure with the valve stable and closed (about 1.7 cm H2O) can be less than about 1 cm H2O higher than the delivered average mask pressure under the constant rotor speed control with the valve stable open (i.e., data points 501, 502 and 504 in FIG. 5B). The delivered average flow at this setting can be within the range of the delivered average flow indicated by data points 501, 502 and 504 in FIG. 5C.

Accordingly, using the illustrated valve and flow generator control combination, the system may move from the sub-therapeutic mode, with a flow generator speed of about 4000 rpm delivering about 0.9 cm H2O, average mask pressure and about 25 liters per minute average flow, to a therapeutic mode, with pressure feedback control, delivering about 1.7 cm H2O average mask pressure and about 20 liters per minute average flow.

When switching from the therapeutic delivery mode to the sub-therapeutic delivery mode (e.g., in response to user awakening), one could expect generally the same transition between system conditions, but in reverse.

Test Results for ResMed Anti-Asphyxia Valve

FIGS. 6A to 6C illustrate the behaviour of the ResMed Quattro valve under constant flow generator speed. This illustrates the way the valve will behave where the flow generator is controlled with slow feedback based on average flow, such as in the preferred sub-therapeutic mode according to certain features, aspects and advantages of the present invention. FIG. 6A illustrates the observed valve state in each of the tests. FIG. 6B indicates the average measured pressure in each of the tests and FIG. 6C illustrates the average measured flow in each of the tests. The sequence of the tests is indicated by the sequence of data points 600, 602,

604, 606, 608, 610, 612, 614, 616. For simplicity, this sequence of data points are indicated by the same reference numerals in each of the FIGS. 6A, 6B and 6C.

From FIG. 6A, it can seen that the behaviour of the ResMed Quattro valve when commencing in the open state remains stable in the open state at blower speeds of 3000 rpm, 4000 rpm, 5000 rpm (data points, 600, 602 and 604). At these blower speeds, the pressure delivered to the artificial lung is approximately 1 cm H2O (data points 600, 602 and 604 in FIG. 6B). The delivered flow at 4000 rpm is about 20 liters per minute and the delivered flow at 5000 rpm is about 30 liters per minute. However, the delivered flow at 3000 rpm is only about 10 liters per minute, which is lower than desirable. Accordingly, the average flow rate across the range of flow generator speed at which the ResMed Quattro valve is stable is approximately 10 liters per minute to 30 liters per minute compared to approximately 15 liters per minute to 35 liters per minute for the valve of FIGS. 9A-9C.

Referring to FIGS. 6D to 6F, these figures illustrate the results of testing in the pressure feedback mode. With reference to data points 620, 622, 624, 626, the ResMed Quattro valve exhibits unstable behaviour with the pressure feedback control at a 1 cm H2O set pressure whether commencing at this set pressure or returning to this set pressure from a higher set pressure. The valve remains unstable at 1.5 cm H2O set pressure (data points 622 and 626 in FIG. 6A). The valve exhibits stable behaviour once the set pressure reaches 2 cm H2O (data point 624 in FIG. 6A). With a set pressure of 2 cm H2O, the delivered average pressure was about 2.2 cm H2O (data point 624 in FIG. 6E). At 2 cm H2O, the delivered average flow rate was about 15 liters per minute (data point 624 in FIG. 6F).

Performance of the ResMed Valve in Combination with the Preferred Control Mode

The delivered average mask pressure with the ResMed Quattro valve at the lowest set pressure for stable closed valve behaviour is approximately 1.2 cm H2O above the delivered average mask pressure under constant speed control with the valve open. The delivered average flow rate is at the lower end of the average flow rate range using motor speed control.

Using this valve and flow generator combination, one could expect to transition from the sub-therapeutic mode (i.e., with a flow generator speed of about 4000 rpm), delivering about 1 cm H2O average mask pressure and about 20 liters per minute average flow, to a therapeutic mode with pressure feedback control, delivering about 2.2 cm H2O mask pressure and about 15 liters per minute average flow. When switching from a therapeutic delivery to the sub-therapeutic delivery, one could expect the same transition between system conditions but in reverse.

Comparison of FIGS. 9A-9C Valve Performance with ResMed Valve Performance

Both the valve of FIGS. 9A-9C and the ResMed valve provide adequate performance in conjunction with the preferred control—switching from an open loop control to a pressure feedback control—at the transition from sub-therapeutic to therapeutic modes. In each case, the delivered flows at the transition are sufficient and the pressure step is reduced compared with the same transition under pressure feedback only control. However, the valve of FIGS. 9A-9C provided a lower step in mask pressure (e.g., about 0.8 cm H2O) when compared with the ResMed valve (e.g., about 1.2 cm H2O) and provided a greater flow at both the sub-therapeutic and the therapeutic pressures around the transition.

Comparison Using the Example Control Method in a Sequence of Simulated Breaths

The effect of particular valve behaviour can be seen in the results of the additional test sequence executed on each of the ResMed Quattro valve and the valve of FIGS. 9A-9C. According to the second test sequence, the artificial lung was set up to simulate continuous breathing at 1000 ml tidal volume, with all breaths sinusoidal at 15 breaths per minute with a one-to-one expiration to inspiration ratio. The flow generator was controlled to commence with a constant speed of 3000 rpm. After a period of time, the flow generator was switched to a pressure feedback mode with a set pressure of 1.5 cm H2O. Throughout the test, the valve behaviour was observed and the delivered flow (i.e., the flow leaving the flow generator) and the pressure at the artificial lung were recorded.

Figure 7A:
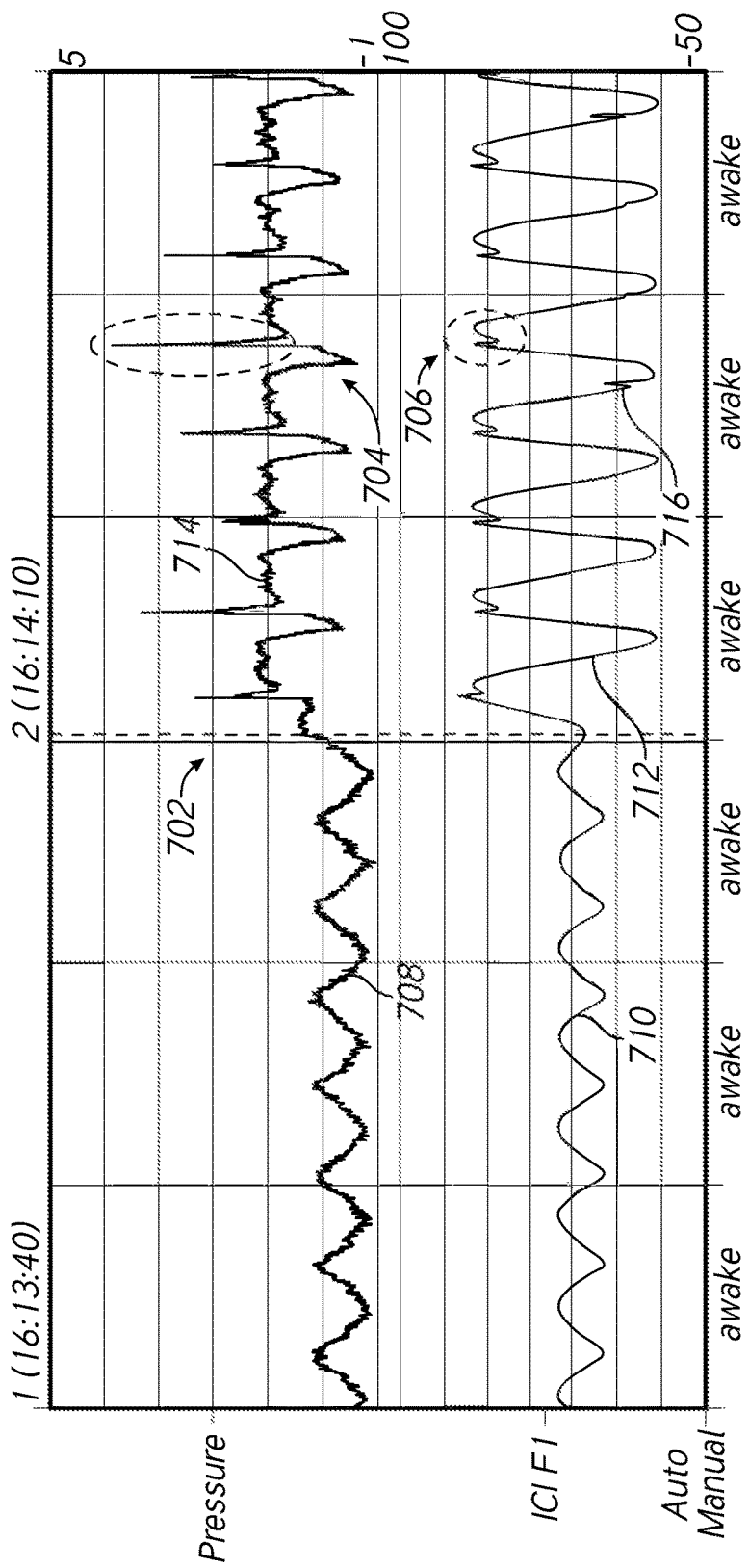
FIGS. 7A and 7B are plots that show flow and pressure versus time for each of two valves and illustrate differences in the valve characteristic between the two valves.
Figure 7B:
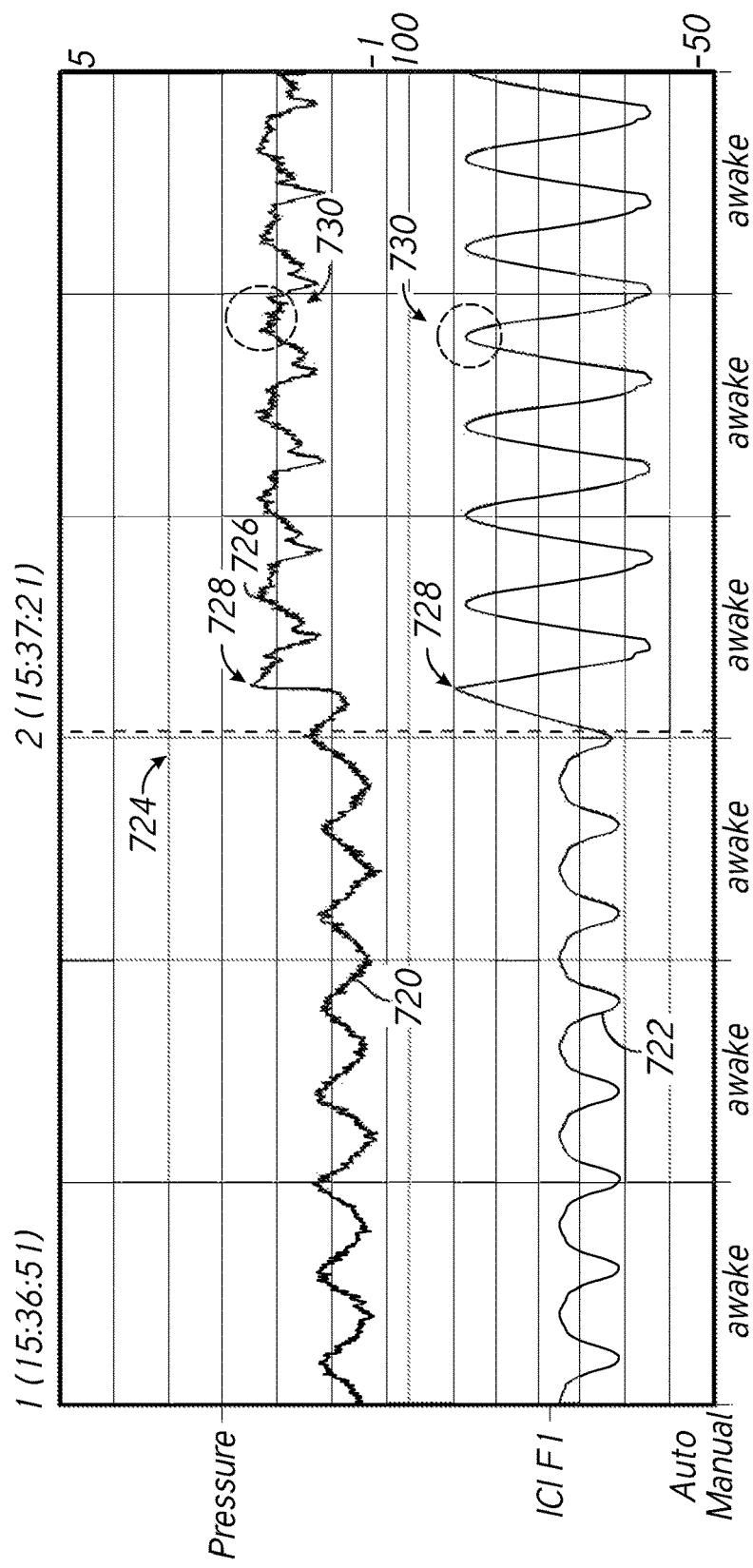

FIG. 7A plots the pressure and flow versus time for the ResMed Quattro valve. FIG. 7B plots the pressure and flow versus time for the valve of FIGS. 9A-9C.

Referring in particular to FIG. 7A, the pressure plot shows a first portion 708 while the flow generator is in constant speed mode and a second portion 714 after the flow generator transitions to pressure feedback mode with a set pressure of 1.5 cm H2O at time 702. With the flow generator in constant speed mode at portion 708, the pressure fluctuates with the sinusoidal breathing pattern imposed by the artificial lung. After the transition to pressure feedback mode, the pressure feedback control is trying to assert control over the pressure and reduces the influence of the imposed breathing.

In the flow plot, portion 710 precedes the transition 702 and portion 712 is after the transition 702. In portion 710, the flow fluctuates with user breathing approximately opposing the fluctuation of pressure. As the artificial lung exhales, the pressure rises and the delivered flow reduces. As the artificial lung inhales, the pressure drops and the delivered flow increases.

After the transition 702, the delivered flow 712 remains in phase with the user breathing. The delivered pressure 714 is more complex, as the feedback control tries to respond to the instantaneous pressure.

One feature of these plots is that the set pressure of 1.5 cm H2O has not been sufficient to bring this valve into a stable, closed condition. This is illustrated by the highlighted spikes 704 in the pressure plot and the highlighted irregularity 706 in the flow plot. The spike 704 and the irregularity 706 occur in each breath in the sequence after entering the pressure feedback mode. The spikes and irregularities indicate that the valve is unstable at 1.5 cm H2O and correspond with the valve snapping shut. The valve then reopens at some point in the cycle and snaps shut again at the start of the next exhalation.

FIG. 7B shows similar plots for the valve illustrated in FIGS. 9A-9C. Again, the plots include portions 720, 722 prior to a transition 724 to the pressure feedback control with a set pressure of about 1.5 cm H2O. For this valve, the difference in average pressure between the period 720 prior to the transition 724 and the period 726 after the transition 724 is lower than the difference in average pressure during the period 708 and average pressure in period 714 for the ResMed Quattro valve. Despite this, the valve of FIGS. 9A-9C has entered a stable closed condition at moment 728 and, as indicated at 730, there are no conspicuous spikes in the pressure plot and no significant discontinuity peaks or irregularities of the flow curve. This corresponds with the observation that the valve had entered a stable, closed condition.

Thus, the valve of FIGS. 9A-9C outperforms the ResMed anti-asphyxia valve by achieving stable closed behaviour at a lower delivered pressure and with a smaller increase in system conditions from a stable open condition.

Figure 8A:
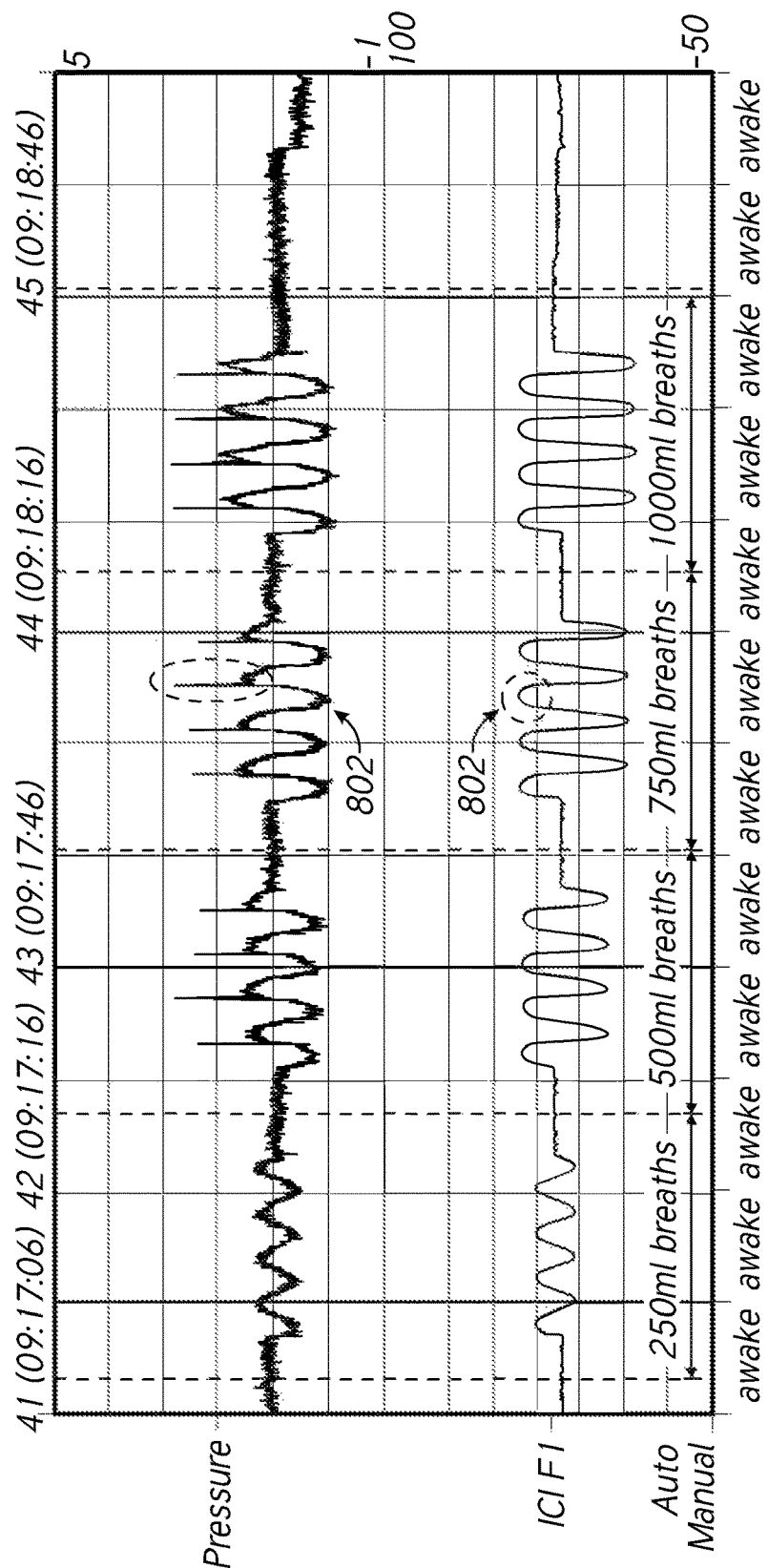
FIGS. 8A and 8B are plots that show flow and pressure versus time that illustrate differences between operating in a flow control mode when the valves are on the verge of closing and operating in a pressure control mode.
Figure 8B:
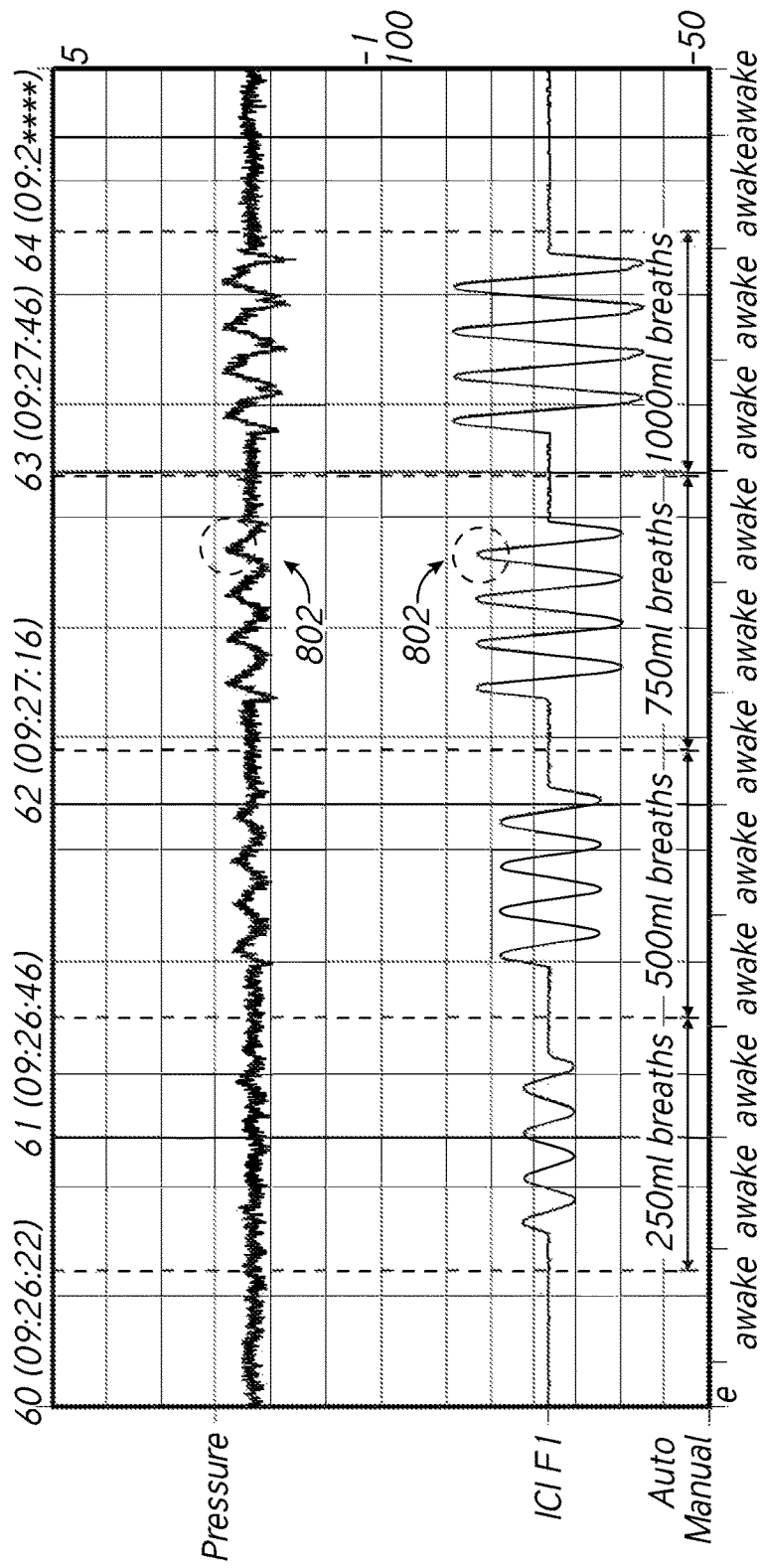

FIGS. 8A and 8B illustrate different characteristics under open loop control and under pressure feedback control for the valve of FIGS. 9A-9C. FIG. 8A illustrates features that correspond to valve instability. FIG. 8B illustrates the effect of pressure feedback on flow fluctuation. Both FIG. 8A and FIG. 8B relate to the valve in the closed state. The sequence was run firstly with the flow generator controlled to have a constant rotor speed of 5000 rpm. In the second test, the flow generator was operated in a pressure feedback mode with a set pressure of 1.5 cm H2O.

The behaviour of the valve of FIGS. 9A-9C was observed in the two modes. Furthermore, the flow and pressure were recorded throughout the tests.

FIG. 8A provides flow and pressure versus time plots for the test conducted with open loop control and with the CPAP speed controlled at 5000 rpm. FIG. 8B shows the pressure and flow versus time plots with pressure feedback control and with the CPAP flow generator pressure set to about 1.5 cm H2O.

FIG. 8A illustrates that the illustrated valve is becoming unstable with a blower speed at 5000 rpm having previously been higher. Instability in FIG. 8A is indicated by the pressure spike 802 becoming apparent in the early part of expiration in each breath.

This can be compared with the performance of the valve recorded in FIG. 8B in the pressure control mode. In the pressure control mode, with a set pressure of 1.5 cm H2O, there are no large transient peaks in the pressure curve, indicating that the valve is stable. However, the peak to peak flow fluctuation is much greater than the flow fluctuation in the open loop control mode illustrated in FIG. 8A.

Overview of Operating Characteristics of Flow Diversion Device and Control Techniques Desirably, the flow diversion device and the control of the flow generator work in cooperation with one another. In some configurations, with the flow generator not generating flow, the user will inhale ambient air through the port of the flow diversion device and exhale air mostly out to ambient through the port. During exhalation, some small portion of the exhaled gases may push the valve member to bend the valve member downward toward the flow generator and a small portion of the exhaled gases may travel down the conduit beyond the valve member.

In some configurations, with the flow generator generating a sub-therapeutic flow of gases (i.e., flow control mode), the user will inhale mostly ambient air through the port while the flow from the flow generator bends the valve slightly toward the user and, as such, provides a small portion of flow to the user. During exhalation, most of the exhalation passes through the port with some portion of the exhalation moving the valve member back toward the flow generator, which slows the flow from the flow generator. Dependent upon the exhalation flow from the user, the flow rate from the user may vary. Thus, the varying flow rate may be indicative of the user breathing, which enables the controller 224 to monitor breathing patterns and identify events (e.g., apnea).

In some configurations, with the flow generator generating a therapeutic flow of gases (i.e., pressure control mode), during inhalation, the valve member overlies the port and the user breathes gases from the flow generator. During exhalation, the user breathes against the flow from the flow generator and the valve member overlies the port.

Although certain features, aspects and advantages of the present invention have been described in terms of a certain embodiments, other embodiments apparent to those of ordinary skill in the art also are within the scope of this invention. Thus, various changes and modifications may be made without departing from the spirit and scope of the invention. For instance, various components may be repositioned as desired. In addition, certain features, aspects and advantages of the invention have been described with reference to breathing gases supply devices particularly for use in the treatment of obstructive sleep apnea. PAP devices also are used in the treatment of other conditions, such as COPD, and may be used for the supply of mixed gases other than air, for example, a mixture of air and oxygen, or a mixture of nitrogen and oxygen or the like. The method and apparatus of the present invention may be equally applied to gas supply apparatus for use in these other treatments. Moreover, not all of the features, aspects and advantages are necessarily required to practice the present invention. Accordingly, the scope of the present invention is intended to be defined only by the claims that follow.

What is claimed is:

1. An apparatus comprising:
a flow generator,
a controller connected to the flow generator to control output of the flow generator,
a conduit extending from the flow generator to connect with a user interface, an inside of the conduit and an inside of the user interface defining a gases space, and
a valve positioned at or adjacent the user interface and in a flow path between the flow generator and a user, the valve being switchable between a first mode in which the gases space is significantly open to ambient through the valve and a second mode in which the gases space is not significantly open to ambient through the valve, the valve including a valve member, a flow passage at least partially defined by a wall, and a gap between the valve member and the wall, wherein the valve is not actively controlled by the controller and wherein the valve is configured to be responsive to change in the output of the flow generator;
the controller comprising one or more positive airway pressure support modes in which the controller is adapted to cause the flow generator to deliver pressure support to an airway of a user with the valve in the second mode, and
the controller comprising one or more sub-therapeutic modes in which the controller is adapted to cause the flow generator to deliver flow of gases to the user with the valve in the first mode,
wherein, with the valve in the first mode and the controller operating in the sub-therapeutic mode, the valve remains stable for flows up to at least about 20 liters per minute with delivered pressures below about 2 cm H2O.

2. The apparatus of claim 1, wherein the valve includes an aperture communicating the gases space with ambient and a valve member that in a second position substantially closes the aperture and is substantially out of a flow path of gases through an portion of the gases space in which the valve is position, and the valve member in a first position leaving the aperture substantially open for substantially unimpeded flow from the user interface to ambient.

3. The apparatus of claim 2, wherein in the first position the valve member partially, but not fully, occludes flow from the flow generator to the user interface.

4. The apparatus of claim 3, wherein the valve member, when in the first position, occludes between about 50% and about 80% of a cross-sectional area of a flow path from the flow generator to the user interface.

5. The apparatus of claim 1, wherein the first position of the valve comprises a valve member of the valve being bent towards the user interface when the user is inhaling.

6. The apparatus of claim 1, wherein the first position of the valve comprises a valve member of the valve being bent towards the flow generator when the user is exhaling.

7. The apparatus of claim 1, wherein the one or more positive airway pressure support modes comprises a supply of gases to the user such that, with the valve in the first mode, the flow generator provides enough flow to the user interface such that, with the user interface worn by a user, a pressure greater than about 3 cm H2O is produced.

8. The apparatus of claim 1 including a sensor adapted to derive a measure of pressure in the gases space such that, in a positive airway pressure mode, the controller controls output of the flow generator according to a command pressure and feedback from the sensor.

9. The apparatus of claim 1, wherein, in the one or more sub-therapeutic modes, the controller controls output of the flow generator to provide a flow to the user interface that is not sufficient to force the valve into the second mode.

10. The apparatus of claim 9 wherein, in the one or more sub-therapeutic modes, the controller causes the flow generator to provide a flow greater than about 5 liters per minute.

11. The apparatus of claim 9, wherein, in the one or more sub-therapeutic mode, the controller causes the flow generator to provide a flow less than about 20 liters per minute.

12. The apparatus of claim 1, wherein the valve moves from the first mode to the second mode upon rising through a first threshold of flow/pressure, and from the second mode to the first mode on falling through a second threshold of flow/pressure, wherein the first threshold of flow/pressure is higher than the second threshold of flow/pressure.

13. The apparatus of claim 1, wherein, with the valve in the second mode and the controller operating in the pressure support mode, the valve remains stable at pressures down to about 3 cm H2O or lower.

14. The apparatus of claim 13, wherein the lowest pressure for which the valve is stable in the second mode when the controller is in the pressure support mode is less than about 1 cm H2O above the average delivered pressure when the valve is in the first mode and the controller is in the one or more sub-therapeutic mode supplying about 15 liters per minute.

15. The apparatus of 1, wherein, in the one or more sub-therapeutic mode, the controller controls the flow generator to deliver an average flow at a level that assures flushing of the user interface but which does not trigger the valve to switch from the first mode to the second mode.

16. The apparatus of 1, wherein the controller controls the flow generator to provide an average flow over multiple breaths that is substantially constant.

17. The apparatus of claim 1, further comprising an aperture in the wall of the conduit between the valve and the user interface, wherein the aperture is located about 5 mm to about 100 mm downstream of the valve.

18. The apparatus of claim 17, wherein the aperture is approximately trapezoidal in perimeter shape with a shorter of two parallel sides being closer to the valve.

19. A valve for use at or adjacent a user interface, the valve comprising:
a flow passage at least partially defined by a wall, the flow passage extending between an inlet and an outlet that is adapted to be fluidly connected to the user interface;
an aperture defined through the wall, the aperture being positioned between the inlet and the outlet; and
a valve member being positioned between the inlet and the aperture, the valve member being movable between a first position and a second position, the valve member in the second position closing the aperture, the valve member in the first position leaving the aperture open for flow to ambient, the valve member in the first position partially but not fully occluding flow through the flow passage, and the valve member in the first position occluding between about 50% and about 80% of a cross section area of the flow passage in a location correlating to the valve member, wherein the valve member is not actively controlled by a controller and wherein the valve member is configured to be responsive to change in the output of a flow generator;
wherein a portion of a perimeter of the valve member and an inner surface of wall is separated by a gap, and
wherein, with the valve in the first position, the valve remains stable for flows up to at least about 20 liters per minute with delivered pressures below about 2 cm H2O.

20. A valve as claimed in claim 19, wherein a cross-sectional area of the flow passage at the location correlating to the valve member is between about 350 mm2 and about 600 mm2.

21. A valve as claimed in claim 20, wherein the area of the aperture is between about 10% and about 50% of the cross sectional area of the flow passage at the location correlating to the valve.

22. A valve as claimed in claim 21, wherein the area of the aperture is between about 15% and about 25% of the cross sectional area of the flow passage through the valve.

* * * * *